(12) United States Patent
Silver

(10) Patent No.: US 7,033,322 B2
(45) Date of Patent: Apr. 25, 2006

(54) IMPLANTABLE SENSOR

(76) Inventor: James H. Silver, 2894 Briarfield Ave., Redwood City, CA (US) 94061

( * ) Notice: Subject to any disclaimer, the term of this patent is extended or adjusted under 35 U.S.C. 154(b) by 454 days.

(21) Appl. No.: 10/041,036

(22) Filed: Nov. 8, 2001

(65) Prior Publication Data

US 2002/0128546 A1 Sep. 12, 2002

Related U.S. Application Data

(63) Continuation-in-part of application No. 09/571,702, filed on May 15, 2000, now Pat. No. 6,442,413.

(51) Int. Cl.
A61B 5/00 (2006.01)

(52) U.S. Cl. .................. 600/486; 600/505; 600/549; 600/561; 600/345; 600/347; 600/365

(58) Field of Classification Search ............... 600/549, 600/561, 486, 488, 505, 345–350, 365
See application file for complete search history.

(56) References Cited

U.S. PATENT DOCUMENTS

| 4,580,568 | A | | 4/1986 | Gianturco |
| 4,655,771 | A | | 4/1987 | Wallsten |
| 4,739,762 | A | | 4/1988 | Palmaz |
| 4,886,062 | A | | 12/1989 | Wiktor |
| 4,890,620 | A | | 1/1990 | Gough |
| 5,102,417 | A | | 4/1992 | Palmaz |
| 5,183,740 | A | | 2/1993 | Ligler et al. |
| 5,195,984 | A | | 3/1993 | Schatz |
| 5,284,138 | A | | 2/1994 | Kujawski |
| 5,411,551 | A | | 5/1995 | Winston et al. |
| 5,421,955 | A | | 6/1995 | Lau et al. |
| 5,431,160 | A | * | 7/1995 | Wilkins ............... 600/347 |
| 5,433,197 | A | | 7/1995 | Stark |
| 5,443,500 | A | | 8/1995 | Sigwart |
| 5,873,906 | A | | 2/1999 | Lau et al. |
| 5,876,432 | A | | 3/1999 | Lau et al. |
| 5,945,676 | A | | 8/1999 | Khalil et al. |
| 6,015,387 | A | | 1/2000 | Schwartz et al. |
| 6,024,763 | A | | 2/2000 | Lenker et al. |
| 6,053,873 | A | | 4/2000 | Govari et al. |
| 6,206,835 | B1 | | 3/2001 | Spillman, Jr. et al. |
| 6,212,416 | B1 | | 4/2001 | Ward et al. |
| 6,231,516 | B1 | | 5/2001 | Keilman et al. |
| 6,245,296 | B1 | | 6/2001 | Ligler et al. |
| 6,258,026 | B1 | | 7/2001 | Ravenscroft et al. |
| 6,285,897 | B1 | | 9/2001 | Kilcoyne et al. |
| 6,331,163 | B1 | * | 12/2001 | Kaplan ............... 600/486 |
| 6,442,413 | B1 | | 8/2002 | Silver |
| 6,475,235 | B1 | * | 11/2002 | Jayaraman ............... 623/1.15 |
| 6,477,395 | B1 | | 11/2002 | Schulman et al. |
| 6,516,808 | B1 | * | 2/2003 | Schulman ............... 600/365 |
| 6,638,231 | B1 | | 10/2003 | Govari et al. |
| 6,741,877 | B1 | | 5/2004 | Shults et al. |
| 2002/0042562 | A1 | | 4/2002 | Maron et al. |
| 2002/0103424 | A1 | | 8/2002 | Swoyer et al. |

FOREIGN PATENT DOCUMENTS

| WO | WO 99/26530 | 3/1999 |
| WO | WO 99/34731 | 7/1999 |
| WO | WO 00/74557 A1 | 12/2000 |

OTHER PUBLICATIONS

Jonsson, B., "The Economic Impact of Diabetes," Diabetes Care 21 (Suppl. 3): C7–C10 (1998).

(Continued)

Primary Examiner—Robert L. Nasser
(74) Attorney, Agent, or Firm—Knobbe Martens Olson & Bear LLP

(57) ABSTRACT

A sensor is disclosed, for implantation within a blood vessel to monitor an analyte in blood. In one embodiment, the analyte is glucose. A signal indicative of glucose level is transmitted to an external receiver. The signal may also be used to drive an internal or externally worn insulin pump. Methods are also disclosed.

54 Claims, 12 Drawing Sheets

OTHER PUBLICATIONS

"The Effect of Intensive Treatment of Diabetes on the Development and Progession of Long–Term Complications In Insulin–Dependent Diabetes Mellitus," The Diabetes Control and Complications Trial Research Group, New Eng. J. Med. 329: 977–86 (1993).

Wilkins, E., et al., "Glucose Monitoring: State of the Art and Future Possibilities," Med. Engl. Phys., vol. 18(18):273–88 (1996).

Jaffari, S.A et al., "Recent Advances in Amperometric Glucose Biosensors for in vivo Monitoring," Physiol. Meas. 16: 1–15 (1995).

Hall, E., "Biosensors," Prentice–Hall Advanced Reference Series, Englewood Cliffs, NJ (1991).

Armour, J. et al., "Application of Chronic Intravascular Blood Glucose Sensor in Dogs," Diabetes, vol. 39: 1519–26 (1990).

Wilson, G.S. et al., "Progress Toward the Developments of an Implantable Sensor for Glucose," Clin. Chem. 1992 38:1613–7.

Kerner, W. et al., "A Potentially Implantable Enzyme Electrode for Amperometric Measurement of Glucose," Horm. Metab. Res. Suppl. Ser. 20: 8–13 (1988).

Updike, S.J. et al., "Enzymatic Glucose Sensors: Improved Long–Term Performance in Vitro and In Vivo," ASAIO j., 40: 157–163 (1994).

Jaremko, J. et al., "Advances Towards the Implantable Artificial Pancreas for Treatment of Diabetes," Diabetes care, 21(3): 444–450 (1998).

Scavani, M. et al., "Long–Term Implantation of a New Implantable Programmable Insulin Pump in Two Diabetic Dogs," Artif. Organs, 16: 518–22 (1992).

Waxman, K. et al., "Implantable Programmable Insulin Pumps for the Treatment of Diabetes," Arch. Surg., 127: 1032–37 (1992).

Irsigler, K. et al., "Controlled Drug Delivery in the Treatment of Diabetes Mellitus," Critical Reviews in Therapeutic Drug Carrier Systems, vol. 1(Issue 3): 189–280 (1985).

Colombo, A. et al., "Intracoronary Stenting Without Anticoagulation Accomplished with Intravascular Ultrasound Guidance," Circulation vol. 91: 1676–88 (1995).

Goldberg, S. et al., "Benefit of Intracoronary Ultrasound in the Deployment of Palmaz–Schatz Stents", J. Am. Coll. Card. vol. 24: 996–1003 (1994).

Virmani, R. et al., "Histopathologic Evaluation of an Expanded Polytetrafluoroethylene Nitinol Stent Endoprosthesis in Canine Iliofemoral Arteries," JVIR, vol. 10, No. 4: 445–456 (1999).

Bates, J. B. et al., "Thin Film Rechargeable Lithium Batteries for Implantable Devices," ASAIO Journal., 43: M644–M647 (1997).

Erickson, K. A. et al., "Evaluation of a Novel Point–of–Care System, the I–Stat Portable Clinical Analyzer," Clin. Chem. 39(2): 283–287 (1993).

Updike, S.J. et al., "The Enzyme Electrode," Nature, vol. 214: 986–8 (1967).

Clark, L.C. et al., "Electrode Systems for Continous Monitoring in Cardiovascular Surgery," Ann. NY Acad. Sci., 102: 29–45 (1962).

Bindra, D. S. et al., "Design and in Vitro Studies of a Needle–Type Glucose Sensor For Subcutaneous Monitoring," Anal. Chem., 63: 1692–6 (1991).

Moussy, F. et al., "Performance of Subcutaneously Implanted Needle–Type Glucose Sensors Employing a Novel Trilayer Coating," Anal. Chem., 65: 2072–7 (1993).

Davies, M.L., et al., "Polymer Membranes in Clinical Sensor Applications, I An Overview of Membrane Function," Biomaterials, 13: 971–89 (1992).

Pan, M., et al. "Simple and Complex Stent Strategies for Bifurcated Coronary Arterial Stenosis Involving the Side Branch Origin," Am. J. Cardiol., 83: 1320–25 (1999).

* cited by examiner

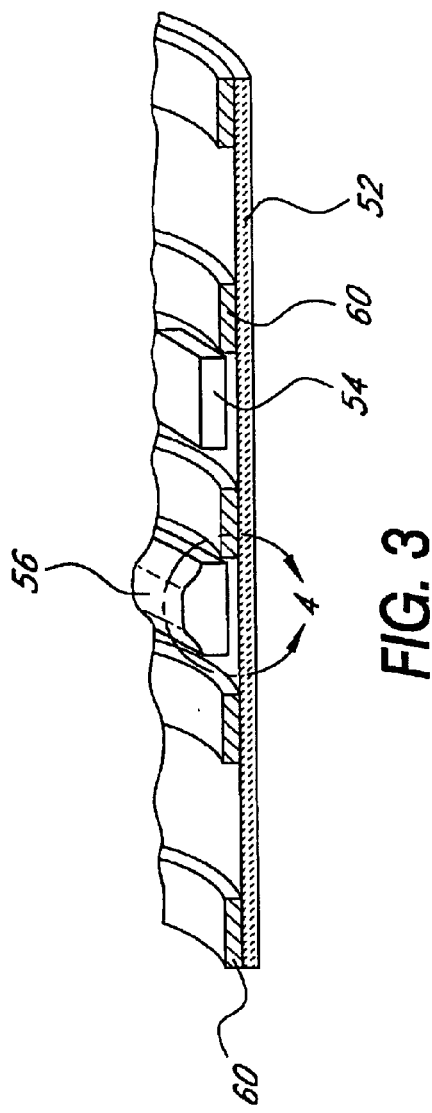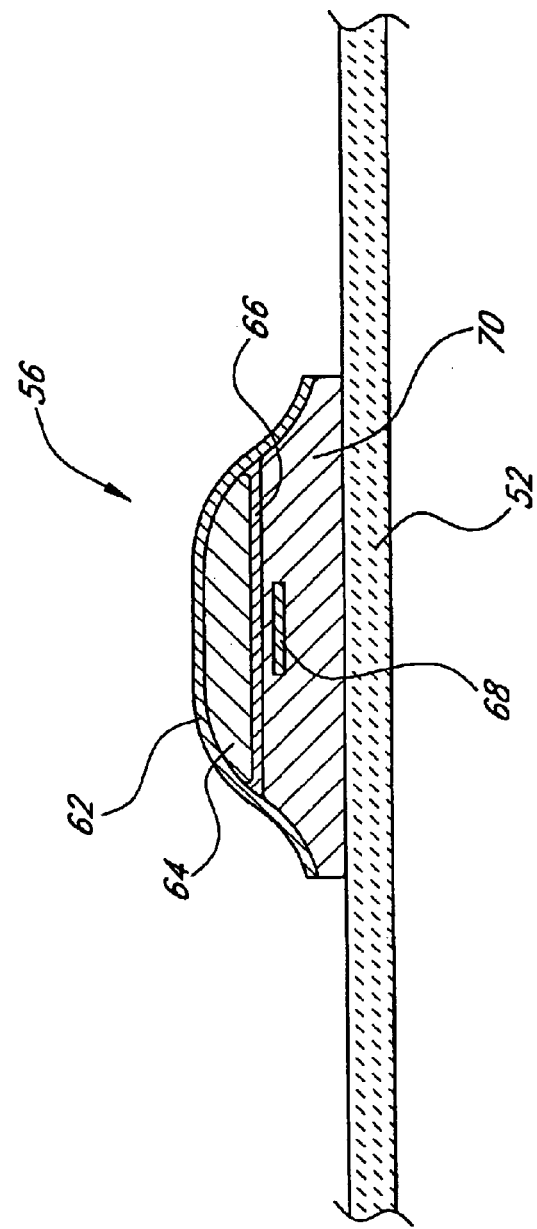

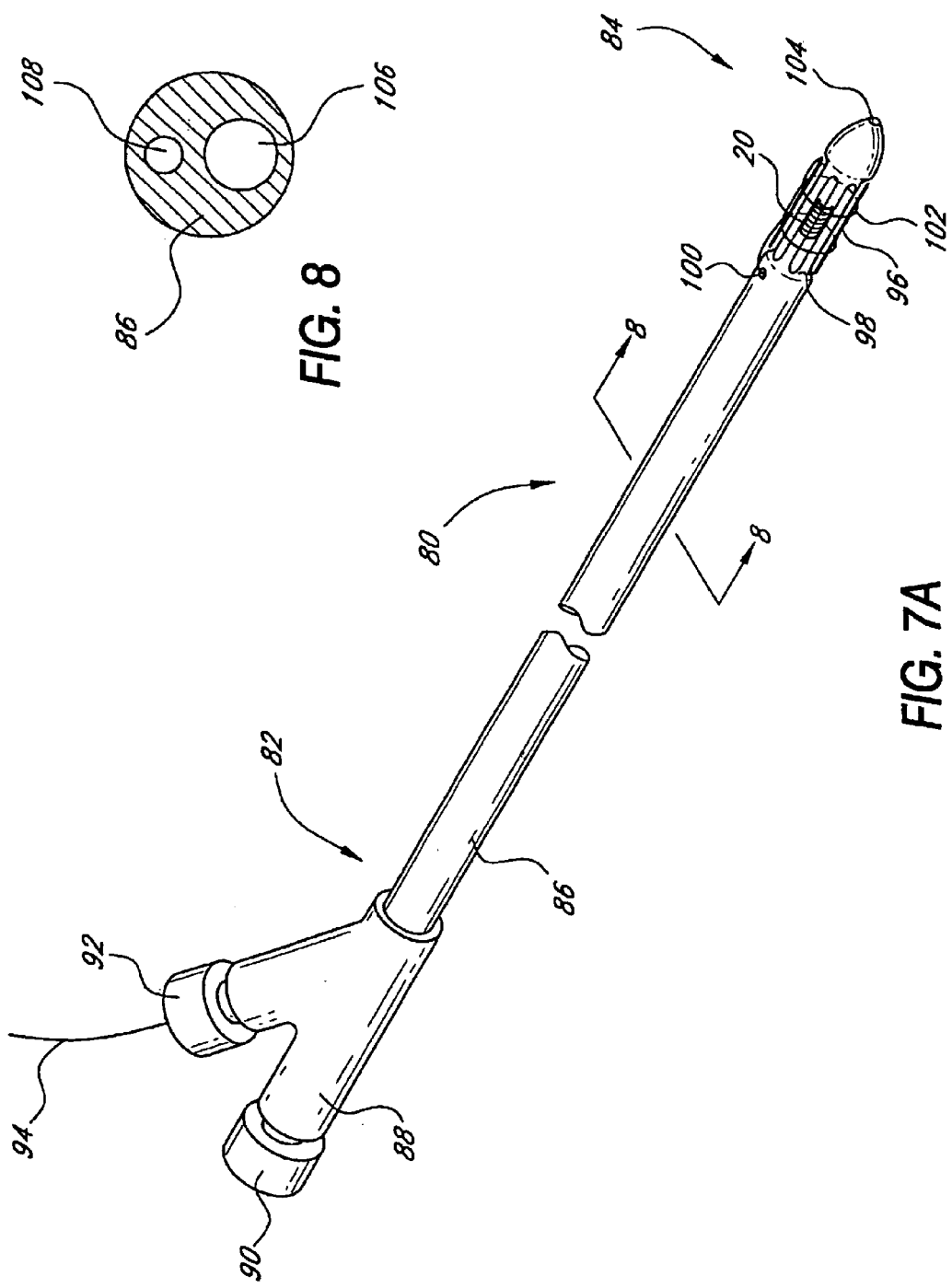

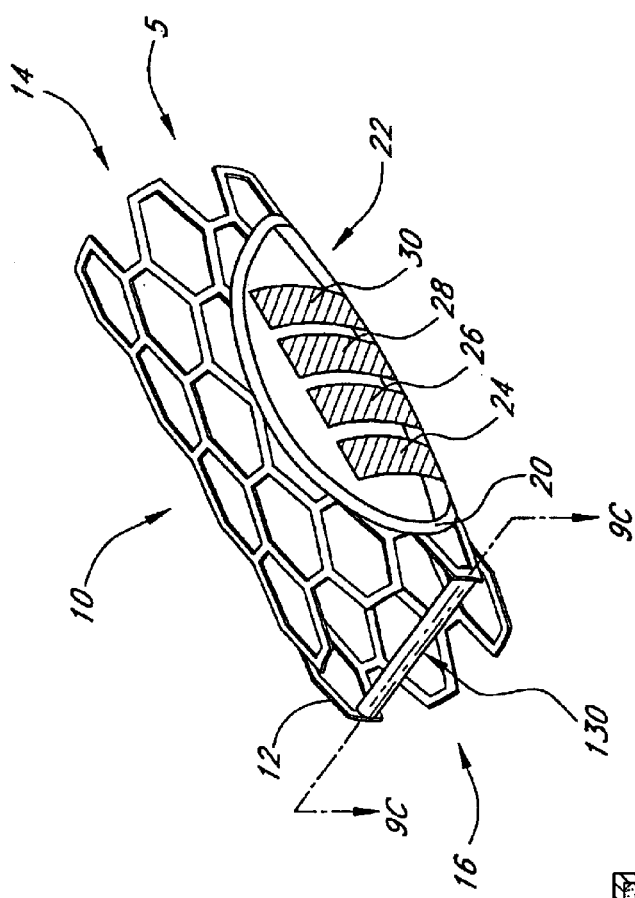
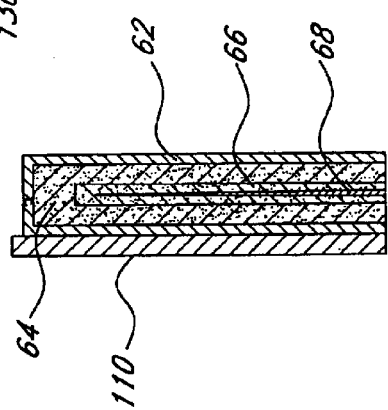
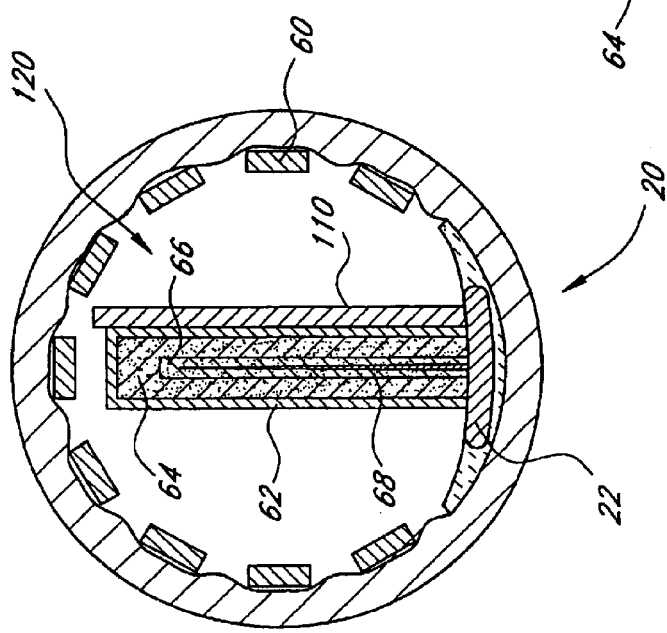
FIG. 9B
FIG. 9C
FIG. 9A

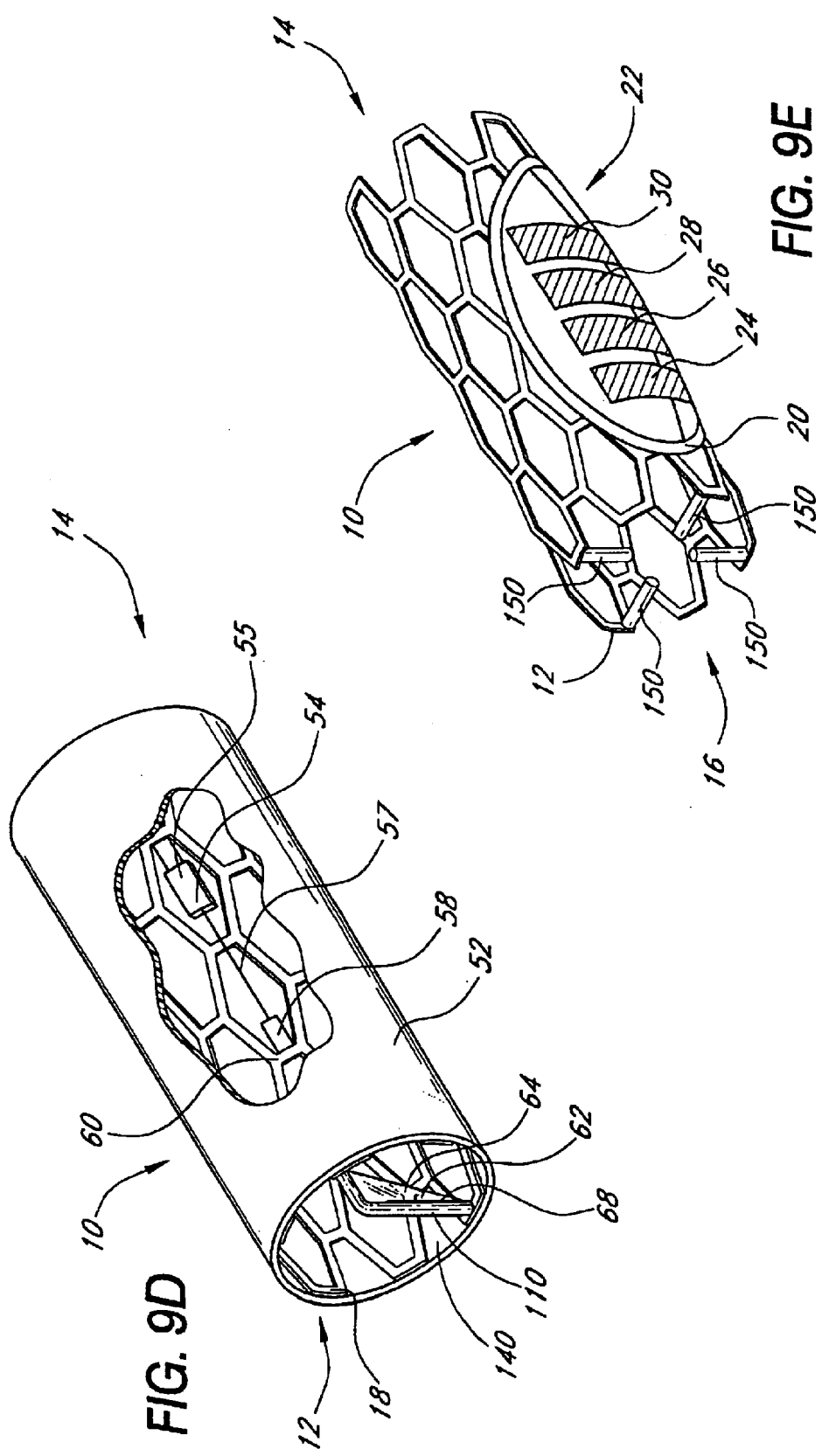

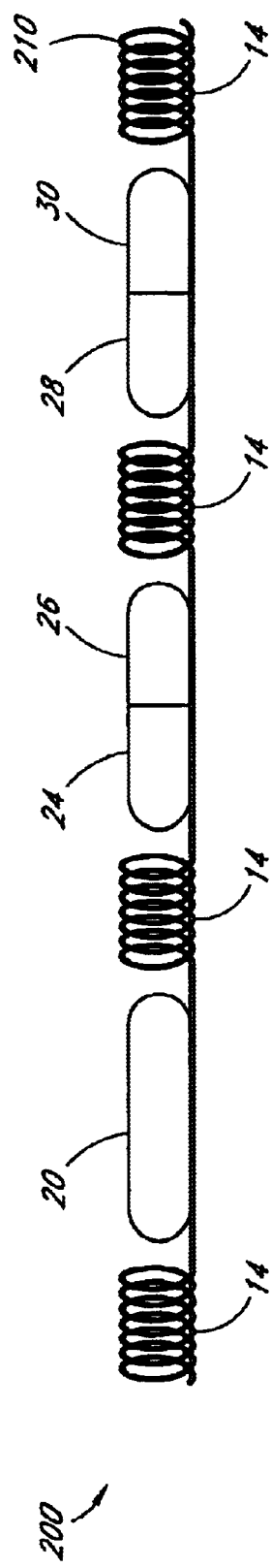

IMPLANTABLE SENSOR

This is a continuation-in-part of U.S. patent application Ser. No. 09/571,702, filed May 15, 2000, now U.S. Pat. No. 6,442,413 issued on Aug. 27, 2002.

BACKGROUND OF THE INVENTION

1. Field of the Invention
2. Description of the Related Art

The present invention generally relates to the use of sensors to monitor the concentration of a chemical species in bodily fluids. More specifically, the present invention relates to the use of sensors to monitor glucose levels, and/or other parameters in a fluid, including flow rate within a lumen of an endoluminal implant such as a stent or other type of endovascular conduit.

Diabetes mellitus is a serious medical condition affecting approximately 10.5 million Americans, in which the patient is not able to maintain blood glucose levels within the normal range (normoglycemia). Approximately 10% of these patients have insulin-dependent diabetes mellitus (Type I diabetes, IDDM), and the remaining 90% have non-insulin-dependent diabetes mellitus (Type II diabetes, NIDDM). The long-term consequences of diabetes include increased risk of heart disease, blindness, end-stage renal disease, and non-healing ulcers in the extremities. The economic impact of diabetes to society has been estimated by the American Diabetes Association at approximately $45.2 billion annually (Jonsson, B., *The Economic Impact of Diabetes*, Diabetes Care 21(Suppl 3): C7–C10, (1998)).

A major long-term clinical study, the Diabetes Control and Complications Trial, involving 1,441 patients with insulin-dependent diabetes mellitus (Type I diabetes) over a 10-year period from 1984–1993, demonstrated that by intensive therapy (frequent administration of either short- or long-acting insulin), these long-term consequences (retinopathy, nephropathy, and neuropathy) could be reduced ("*The Effect of Intensive Treatment of Diabetes on the Development and Progression of Long-Term Complications in Insulin-Dependent Diabetes Mellitus*," The Diabetes Control and Complications Trial Research Group, New Eng. J. Med., 329: 977–86 (1993)). Unfortunately, a major difficulty encountered during the trial was that intensive treatment also resulted in a higher incidence of low blood glucose levels (hypoglycemia), which was severe enough to result in coma or death, as compared to patients under conventional medical management.

Currently, diabetics must monitor their condition by repeatedly pricking their fingers in order to obtain blood samples for evaluation. The major drawback to self-monitoring of glucose is that it is discontinuous and therefore the number of glucose measurements performed is dependent on the motivation of the patient.

Existing analytical techniques and devices for in vitro glucose measurements have a high level of accuracy (the error can be <1%). Many of these routine methods are accepted as standards of comparison with new devices. Management of diabetes currently relies on these methods to control the disease and minimize complications.

There are two main disadvantages to these existing options. First, sampling even a minimal amount of blood multiple times per day is associated with risks of infection, nerve and tissue damage, and discomfort to the patients. Second, in the case of dynamic changes in glucose concentration, very frequent or even continuous measurements of blood glucose levels are required (Wilkins, E., et al., "*Glucose Monitoring: State of the Art and Future Possibilities*", Med. Eng. Phys. 18(4):273–88, (1996).

There are two main approaches to the development of a continuous blood glucose monitor. The first category is non-invasive sensors, which obtain information from physico-chemical characteristics of glucose (spectral, optical, thermal, electromagnetic, or other). The second category is invasive sensors. In this group, there is intimate mechanical contact of the sensor with biological tissues or fluids, since the device is placed within the body. (Wilkins, 1996).

Non-invasive sensor technology has focused on the absorption of the near-infrared (NIR) spectra by the analyte, in this case, glucose (See U.S. Pat. No. 5,945,676 to Khalil, et al., and U.S. Pat. No. 5,433,197 to Stark). Absorptions which occur in the NIR region are most often associated with overtone and combination bands of the fundamental vibrations of —OH, —NH, and —CH functional groups. As a result, most biochemical species will exhibit some absorption in the region of interest. Glucose measurements are usually performed in the spectra region from 4250 to 660 $cm^{-1}$. These highly overlapping, weakly absorbing bands were initially thought to be too complex for interpretation and too weak for practical application. Improvements in instrumentation and advances in multivariate chemometric data analysis techniques may allow meaningful results to be obtained from these complex spectra.

However, to date these devices are not particularly accurate even in the normal physiological range. A subject-dependent concentration bias has been reported. The temperature sensitivity of water absorption bands in the glucose-measuring region can be a significant source of error in clinical assays. In addition, the devices can also be affected by individual variations between patients at the measurement site. Skin location, temperature and tissue structure may affect the results, and decrease the accuracy of the reading.

Other investigators have looked into measurement of glucose from body fluids other than blood, such as sweat, saliva, urine, or tears. However, factors relating to diet and exercise can affect glucose levels in these fluids. In general, there is no strong correlation established between glucose concentration in the blood and in excreted fluids. The lag time between blood and excreted fluid glucose concentrations can be large enough to render such measurements inaccurate.

The continuous in vivo monitoring of glucose in diabetic subjects should greatly improve the treatment and management of diabetes by reducing the onus on the patient to perform frequent glucose measurements. Implanted glucose sensors could be used to provide information on continuously changing glucose levels in the patient, enabling swift and appropriate action to be taken. In addition, daily glucose concentration measurements could be evaluated by a physician. An implantable sensor could also provide an alarm for hypoglycemia, for example, overnight, which is a particular need for diabetics. Failure to respond can result in loss of consciousness and in extreme cases convulsive seizures. Similarly, a hyperglycemic alarm would provide an early warning of elevated blood glucose levels, thus allowing the patient to check blood or urine for ketone bodies, and to avert further metabolic complications. (Jaffari, S. A. et al., "Recent Advances In Amperometric Glucose Biosensors For In Vivo Monitoring", Physiol. Meas. 16:1–15 (1995)).

Invasive glucose sensors may be categorized based on the physical principle of the transducer being incorporated.

Current transducer technology includes electrochemical, piezoelectric, thermoelectric, acoustic, and optical transducers.

In piezoelectric, thermoelectric, and acoustic (surface acoustic wave, SAW) sensors used for glucose measurement, an enzyme-catalyzed reaction is used to create a measurable change in a physical parameter detected by the transducer. The development of these sensors is at an early laboratory stage (Hall, E.; *Biosensors*, Oxford University Press. Oxford, 1990). Optical sensors are based on changes in some optical parameter due to enzyme reactions or antibody-antigen reactions at the transducer interface. Based on the nature of the monitoring process, they are densitometric, refractometric, or colorimetric devices. At present, none of them meets the selectivity requirements to sense and accurately measure glucose in real physiological fluids.

There is a significant body of literature regarding the development of electrochemical glucose sensors. These generally incorporate an enzyme, which selectively reacts with glucose. Examples of enzymes, which selectively react with glucose, are glucose oxidase (GOD), hexokinase, glucose-6-phosphate dehydrogenase (G-6-PD), or glucose dehydrogenase. Hexokinase is an enzyme that catalyzes the phosphorylation of glucose by ATP to form glucose-6-phosphate and ADP.

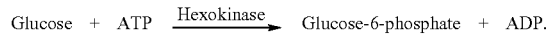

$$\text{Glucose} + \text{ATP} \xrightarrow{\text{Hexokinase}} \text{Glucose-6-phosphate} + \text{ADP}.$$

Monitoring the reaction requires a second enzyme, glucose-6-phosphate dehydrogenase, in the following reaction:

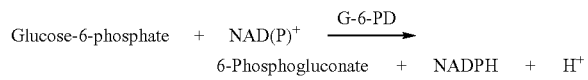

$$\text{Glucose-6-phosphate} + \text{NAD(P)}^+ \xrightarrow{\text{G-6-PD}} \text{6-Phosphogluconate} + \text{NADPH} + \text{H}^+$$

The formation of NADPH may be measured by absorbance at 340 nm or by fluorescence at 456 nm (Jaffari, 1995).

Glucose dehydrogenase is another enzyme, which may be used for monitoring glucose in the following reaction:

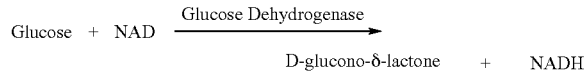

$$\text{Glucose} + \text{NAD} \xrightarrow{\text{Glucose Dehydrogenase}} \text{D-glucono-}\delta\text{-lactone} + \text{NADH}$$

The NADH generated is proportional to the glucose concentration.

Glucose oxidase is the most commonly used enzyme reported in the literature. Its reaction is relatively simple, inexpensive, and may be monitored using a variety of techniques.

These advantages have led to the extensive use of this enzyme in clinical analysis as well as its incorporation in the majority of prototype biosensor configurations. The reaction of glucose with this enzyme is a two-stage reaction:

1) -D-glucose+GOD(FAD)→glucono-δ-lactone+GOD(FADH$_2$)
2) GOD(FADH$_2$)+O$_2$→GOD(FAD)+H$_2$O$_2$
3) glucono-δ-lactone+H$_2$O→gluconic acid The overall reaction is usually expressed as:

4) β-D-glucose+O$_2$+H$_2$O→gluconic acid+H$_2$O$_2$

The reaction can therefore be monitored by the consumption of oxygen, the production of hydrogen peroxide, or the change in acidity due to the increase of gluconic acid.

Despite the foregoing and other efforts in the art, a suitable continuous in dwelling glucose sensor has not yet been developed.

A critical factor in the design of an implanted sensor is the anatomical site in which it is implanted. A few investigators have developed monitoring systems, which can be placed within the vascular system. Armour et al. ("*Application of Chronic Intravascular Blood Glucose Sensor in Dogs*", Diabetes 39:1519–26 (1990)) implanted a sensor into the superior vena cava of six dogs for a period of up to 15 weeks with relative success. However, due to the risks of thrombosis and embolization, the majority of investigators have focused on subcutaneous implantation.

A major drawback to subcutaneous implantation is the body's defense against foreign objects: the "foreign-body response". In this host response, if an object cannot be removed by the inflammatory response, foreign-body giant cells will form a "wall" around the object, which is subsequently followed by the formation of a fibrous capsule. If the object is a blood glucose sensor, it will no longer be in intimate contact with body fluids, and the signal will drift and stability will be lost. There are numerous reports of sensor stability being lost in about a week (Wilson, G. S., et al., "*Progress Towards The Development Of An Implantable Sensor For Glucose*", Clin. Chem. 1992 38:1613–7, and Kemer, et al., "*A Potentially Implantable Enzyme Electrode For Amperometric Measurement Of Glucose*", Horm. Metab. Res. Suppl. Ser. 20: 8–13 (1988)). Updike et al. (Updike, Stuart J., et al., "*Enzymatic Glucose Sensors: Improved Long-Term Performance In Vitro And In Vivo*", ASAIO J., 40: 157–163 (1994)) reported on the subcutaneous implantation of a sensor which was stable for up to 12 weeks, however, this evaluation was only performed in three animals.

Recent clinical studies have also demonstrated that implantable insulin pumps are feasible for implantation for over one year (Jaremko, J. et al., "*Advances Towards the Implantable Artificial Pancreas for Treatment of Diabetes*," Diabetes Care, 21(3): 444–450 (1998)). The research was inspired by the goal of the development of the artificial pancreas, and promising initial clinical trials using implantable insulin pumps. At this point in time, development of implantable insulin pumps is at a very advanced stage, with units being implanted for over 2 years in canines (Scavani et al., "*Long-Term Implantation Of A New Programmable Implantable Insulin Pump*," Artif. Organs, 16: 518–22 (1992)) and in 25 patients for up to 3 years (Waxman, et al., "*Implantable Programmable Insulin Pumps For The Treatment Of Diabetes*", Arch. Surg., 127: 1032–37 (1992)).

A number of wearable insulin pumps are described by Irsigler et al. ("*Controlled Drug Delivery In The Treatment Of Diabetes Mellitus*," Crit. Rev. Ther. Drug Carrier Syst., 1(3): 189–280 (1985)). Thus, it should be relatively straightforward to couple a long-term implantable glucose sensor as described in this disclosure, to an insulin pump to optimize glycemic control for the patient.

Notwithstanding the extensive efforts in the prior art, however, there remains a need for an implantable blood glucose sensor for implantation in a blood vessel, which can provide useful blood glucose readings for an extended period of time, without material interference from thrombus formation, embolization, or other foreign body response. Preferably, the sensor is capable of continuous or near continuous monitoring, and driving an implantable insulin pump and/or making blood glucose data available to the patient or medical personnel.

SUMMARY OF THE INVENTION

The present invention generally relates to the use of sensors to monitor the concentration of a chemical species in bodily fluids, and more specifically, to a novel sensor configuration to monitor glucose levels in a body vessel. The device is an implantable glucose sensor, which is delivered to the patient's vascular system preferably transluminally via a catheter, using a stent or stent-graft as a platform. One feature of the device is that the sensor surface is placed at the apex of the luminal surface of a streamlined housing, so that the shear rate at the sensor/blood interface is sufficient to minimize the thickness of the formed thrombus layer. In this manner, significant tissue deposition or encapsulation due to potential fibrotic reactions is minimized, and transport of glucose to the sensor is not altered over time.

Thus, there is provided in accordance with one aspect of the present invention a blood glucose detector for implantation within a blood vessel. The blood glucose detector comprises a support, having a first side for contacting the wall of the vessel and a second side for facing radially inwardly towards the center of the vessel. A sensor is carried by the support, and the sensor has a sensing surface thereon. The sensing surface is spaced radially inwardly from the first side by a distance of at least about 0.2 to 2.5 mm, such that the velocity of blood in the vessel inhibits obstruction of the sensing surface. Preferably, the distance is at least about 0.5 mm. The blood glucose detector further comprises a transmitter on the support, for transmitting information from the sensor to an external receiver. In one embodiment, the support comprises an expandable tubular body. The tubular body may be either a balloon expandable or a self-expandable component such as a stent. The tubular body may be further provided with a tubular sheath on the radially inwardly directed surface and/or the radially outwardly directed surface. In one embodiment, the sensor comprises an analyte permeable membrane and an enzyme gel layer.

In accordance with another aspect of the present invention, there is provided a method of prolonging the useful life of a sensor in a blood vessel. The method comprises the steps of providing a sensor having an analyte sensing surface thereon, and positioning the sensor at a site in a blood vessel such that the sensing surface is positioned radially inwardly from the vessel wall by a sufficient distance that the blood flow shear rate at the sensing surface substantially delays obstruction of the sensing surface. Preferably, the positioning step comprises carrying the sensor on a catheter and transluminally advancing the catheter to the site.

In accordance with a further aspect of the present invention, there is provided an implantable sensor for sensing the presence of an analyte in a vessel. The sensor comprises a tubular support structure for anchoring the sensor in a vessel. The support has a sidewall with a luminal side facing towards the center of the vessel and an abluminal side facing towards the wall of the vessel. A sensor housing is carried by the support structure, the housing having a streamlined exterior configuration to minimize blood flow turbulence. A power supply and electrical circuitry are provided in the housing, and a sensing surface carried by the housing is exposed to the exterior of the housing. The sensing surface is positioned on the radially inwardly most portion of the luminal side of the housing.

Preferably, the support structure comprises an expandable metal coil or mesh. The sensor housing may be positioned on the luminal side of the support structure or the abluminal side of the support structure.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a cross-section taken along the line 3—3 in FIG. 2.

FIG. 4 is an enlarged cross-sectional view through the sensor element of FIG. 3.

FIG. 7A is a side elevational view of the distal end of a catheter-based delivery system for a stent sensor device.

FIG. 8 is a cross-sectional view of the catheter-based delivery system taken along the 8—8 line of FIG. 7A.

FIG. 9A is a cross-sectional view through a stent showing a transducer across the cross-section of the stent in accordance with the present invention.

FIG. 9B is a perspective view of an expanded stent with an embedded sensor housing on its abluminal side and a transducer across the cross-section of the stent.

FIG. 9C is an enlarged cross-sectional view of the transducer of FIG. 9B, taken from the 9C—9C line.

FIG. 9D is a perspective partial cut away view of a stent sensor device surrounded by a sheath with a transducer partially across the cross-section of the stent.

FIG. 9E is a perspective view of an expanded stent with an embedded sensor housing on its abluminal side and four perpendicular transducers placed partially across the cross-section of the stent.

FIG. 11 shows a side elevational view of a sensor and transmitter, with anchoring stents in the compressed state at the proximal end of the sensor, intermediate between the sensor and transmitter, and at the distal end of the transmitter.

DETAILED DESCRIPTION OF THE PREFERRED EMBODIMENT

Figure 1:
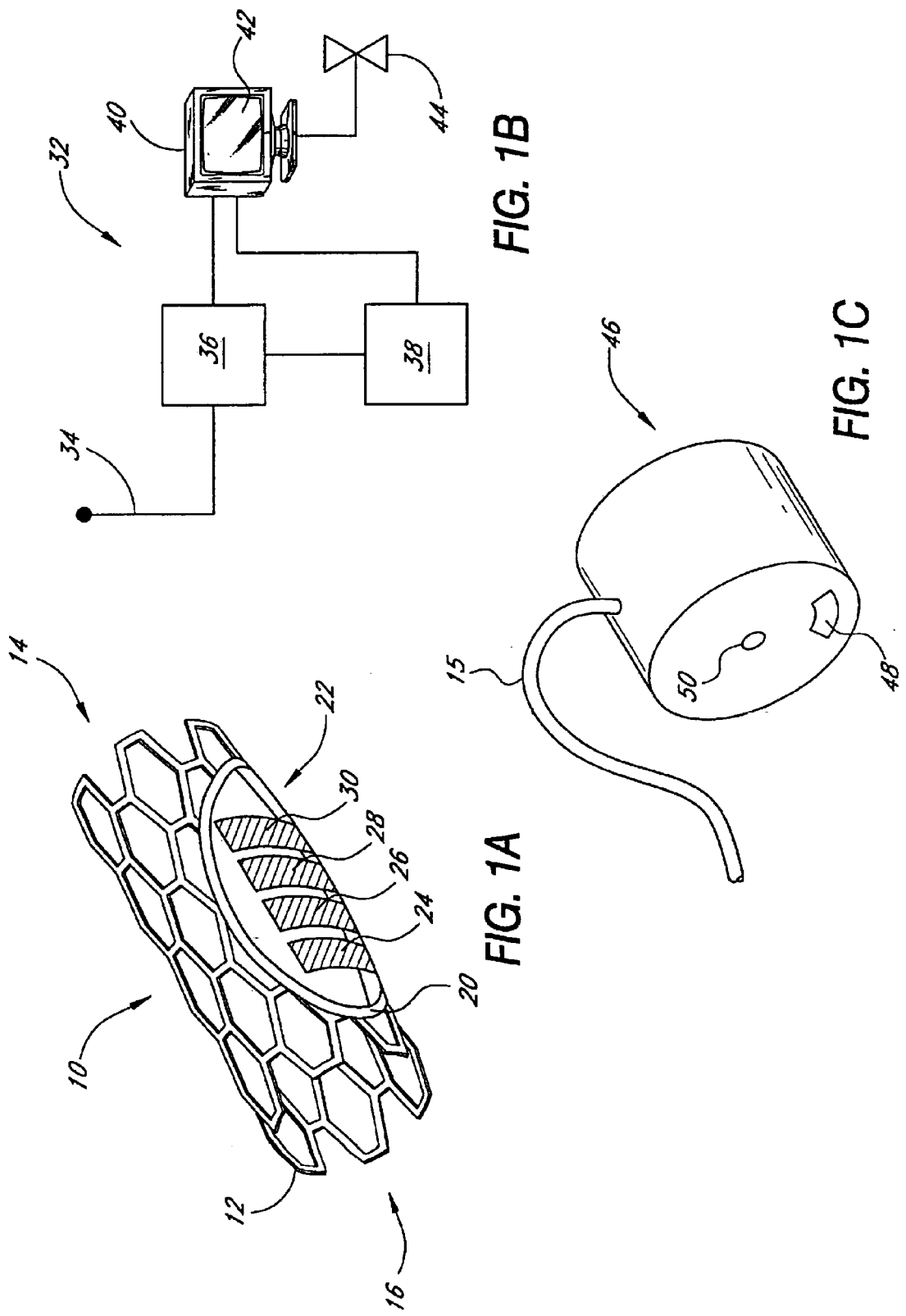
FIG. 1A is a perspective view of an expanded stent with an embedded sensor housing on its abluminal side.
FIG. 1B is a block diagram of remote circuitry for an external monitoring device.
FIG. 1C is a diagram of a wearable or implantable insulin pump.

In accordance with the present invention, an intraluminal blood glucose sensor is provided on a support structure such as a modified stent of the type implanted following percutaneous transluminal coronary angioplasty (PTCA) for the treatment of atherosclerosis. Atherosclerosis is the build-up of fatty deposits or plaque on the inner walls of a patient's arteries. These lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guide wire to a point where the stenotic lesions limit blood flow through the coronary artery. The balloon is then inflated, compressing the lesions radially outward against the wall of the artery and substantially increasing the size of the arterial lumen, to improve blood circulation.

Increasingly, stents are being used in place of or in addition to PTCA for treatment of atherosclerosis, with the intent of minimizing the need to repeatedly open a stenosed artery. Although a number of different designs for stents exist in the prior art, all are generally configured as elongate cylindrical structures that can assume two different states, one having a substantially greater diameter than the other. A stent is implanted in a patient's vascular system using an appropriate delivery system. There are two basic types of stents. The first type is termed "balloon expandable", and refers to stents that are expanded radially outward due to the force from an inflated angioplasty balloon, such as the Palmaz-Schatz stent, the Gianturco-Roubin stent, and the Strecker stent. The second type is termed "self-expandable", and refers to and those that are self-expanding, such as the Hemobahn™ and SMART Stent™ (made of nickel titanium memory alloy), and the Wallstent (made of Elgiloy).

Typically, a stent carried by a delivery catheter is advanced through a guide catheter to a site within the patient's artery. For the balloon expanded type, after the introducer sheath is retracted, a balloon disposed inside the stent is inflated to a pressure ranging from about six to ten atmospheres. The force produced by the inflated balloon expands the stent radially outward beyond its elastic limit, stretching the vessel and compressing the lesion to the inner wall of the vessel. A self-expanding stent expands due to spring force following its positioning within the artery, after a restraining sheath is retracted from the compressed stent. Following the expansion process, if the balloon expandable type is used, the balloon is deflated and removed from inside the stent and the catheter and other delivery apparatus is withdrawn. The lumen through the vessel should be substantially increased, improving blood flow.

After a stent or other endoluminal device is implanted, a clinical examination and either an angiographic or ultrasonographic morphological procedure is performed to evaluate the success of the procedure in opening the diseased artery or vessel. These tests are typically repeated periodically, e.g., at six-month intervals, since restenosis of the artery may occur.

Although the sensor of the present invention may be carried by any of a wide variety of intraluminal support structures, balloon expandable or self-expandable stents are preferred by the present inventor. In general, the stent may be modified from those intended for supporting a treatment site following angioplasty, in view of the preferred placement in a healthy section of the vessel as is discussed in greater detail below. In addition, the wall of the stent may be modified to support the sensor, as is also discussed in greater detail below. As well as providing a useful support structure with known deployment characteristics, a stent provides a useful platform for a variety of additional reasons. For example, it is impractical to pass an electronic conductor through the wall of an artery or vessel to monitor the condition of an implanted sensor for long periods of time. Also, any active glucose sensor must be energized with electrical power. Again, it is not practical to supply power to such a sensor through any conductor that perforates the vessel wall or that passes outside the patient's body.

In addition to stents, the generic term endoluminal implant encompasses stent-grafts, which are also sometime referred to as "covered stents." A stent-graft is a combination of one or more stents and a synthetic graft that is typically implanted at a desired point in a vessel using an endoscopic approach. The stent is attached either to the ends or throughout the body of the synthetic graft, and is used to hold the graft in position. Sometimes, hooks are provided on the stent to ensure that the graft remains in the desired position within the vessel. Clearly, it would also be desirable to monitor the status of glucose and other parameters through a stent graft, just as noted above in regard to a stent.

Endoluminal implants are used in other body passages in addition to blood vessels. For example, they are sometimes used to maintain an open lumen through the urethra, or through the cervix. A stent placed adjacent to an enlarged prostate gland can prevent the prostate from blocking the flow of urine through the urinary tract. Tracheal and esophageal implants are further examples of endoluminal implants. In these and other uses of an endoluminal implant, provision for monitoring parameters related to the status of flow and other conditions in the patient's body would be desirable. Information provided by monitoring such parameters can enable more effective medical treatment of a patient.

A number of factors will affect the function of a glucose sensor implanted within a blood vessel. As with stents, the device should be designed to minimize the risk of thrombosis and embolization. Thus, slowing or stoppage of blood flow at any point within the lumen should be minimized. Colombo et al. ("*Intracoronary Stenting Without Anticoagulation Accomplished With Intravascular Ultrasound Guidance*," Circulation 91:1676–88, (1995)) and Goldberg et al. ("*Benefit Of Intracoronary Ultrasound In The Deployment Of Palmaz-Schatz Stents*", J. Am. Coll. Card. 24:

996–1003, (1994)) demonstrated that one of the key factors resulting in subacute stent thrombosis in coronary arteries was inadequate expansion of the stent. This was done using intravascular ultrasonography (IVUS). Another important factor, and related, is that the stents must be placed in close apposition to the vessel wall, so that the only flow obstructions are at the luminal surface of the stent struts. They later demonstrated that by using non-compliant balloons at high pressure (18 atm), that even the final assessment using IVUS is not required; an important consideration for centers lacking such equipment. Thus, it is very important to minimize flow disturbances which may be created by stent implantation. This is more critical in the smaller coronary arteries, which range from about 2.5–4 mm in diameter, than it is in other, larger arteries, where small amount of mural thrombus will have less effect on the volumetric flowrate.

Usually, a layer of fibrin clot deposits on the luminal surface of the implanted stent. After 3–4 weeks, the fibrin layer is typically remodeled into fibro-collagenous tissue, with a layer of endothelial cells present on the flow surface. However, if a relatively thick layer of fibro-collagenous tissue forms on the surface of an endovascular sensor, it may experience the same loss of signal that has been reported for subcutaneously implanted sensors. That is, a modified type of "foreign-body response" may occur, and glucose may not be able to freely and rapidly diffuse to the sensor. Evaluation of an ePTFE (expanded polytetrafluoroethylene) covered stent graft (Virmani, et al., "*Histopathologic Evaluation Of An Expanded Polytetrafluoroethylene Nitinol Stent Endoprosthesis In Canine Iliofemoral Arteries*," JVIR, 10:445–456 (1999)) showed that in areas where the graft surface was further from the center of the flow channel, it became covered with a relatively thick layer of thrombus, which eventually converted to fibro-collagenous tissue. In areas where the graft surface was closer to the center of the flow channel, it became covered with a relatively thin layer of tissue, and in some cases remained uncovered for periods of up to one year in a canine. Thus, there is a balance between minimizing disruption of blood flow, and excessive thrombus deposition.

Unlike a stent or stent-graft, which is used in the treatment of occlusive or aneurysmal vascular disease, however, the stent-sensor combination of the present invention should be placed in a relatively healthy portion of the artery. If it is placed in a stenotic or calcified area, it may be difficult for the device to expand completely, so the device may be more narrowed than is intended, resulting in thrombotic fouling of the sensor, or distal embolization may occur. If the device is placed in an aneursymal vessel, it may expand more than intended, and again, fail to function as designed.

In addition, some types of sensors require that the actual sensing component be covered with a semi-permeable membrane in order to allow certain components such as glucose to pass through, while excluding cells, enzymes, or other factors which could damage the sensor. Thus, a stent-graft-sensor combination might be more suitable than a stent-sensor combination without the graft material. Further considerations will become apparent from the illustrated embodiments of the present invention which are discussed below.

FIG. 1A shows a perspective view of an expanded implantable sensor device 10 having a proximal end 12, a distal end 5 and a central lumen 16 extending therethrough. The expanded implantable sensor device 10 is comprised of a stent 14 and a sensor 20. Although the stent 14 illustrated in FIG. 1A resembles a Palmaz-Schatz stent, it is understood that any of a wide variety of stent configurations can be utilized such as those identified below. Whether the stent is a balloon expandable or self-expandable variety, the stent 14 comprises a tubular sidewall 18, which may be compressed to a relatively small diameter for delivery using a catheter, and which may be expandable to the approximate diameter of the vessel or to a diameter approximately 5–25% greater than the diameter of the vessel lumen.

In general, a self-expanding variety of stent or stent-graft such as the S.M.A.R.T. Stent (Cordis Corp., Miami, Fla.) or Hemobahn (W.L. Gore & Associates, Flagstaff, Ariz.) is preferred, since the presence of the sensor body may impede proper expansion of the stent platform using a balloon. The sensor housing can preferably be attached to the stent by use of adhesives, by tying (suturing) the two components together, or by use of thermal bonding, soldering, welding or brazing, or mechanical interfit or the like. The sensor and sensor housing should be attached to the stent along a single row of stent struts, so that the struts may fully expand without needing to stretch the sensor housing, or being constrained by the sensor housing.

An example of the type of stent which could be used in certain embodiments of the present invention is described by Lau et al. in U.S. Pat. No. 5,876,432, issued Mar. 2, 1999 which is herein incorporated by reference. Other stents which are suitable for use in the present invention are described by U.S. Pat. No. 4,739,762 to Palmaz, issued Apr. 26, 1988; U.S. Pat. No. 5,102,417 to Palmaz, issued Apr. 7, 1992; U.S. Pat. No. 5,421,955 to Lau et al., issued Jun. 6, 1995; U.S. Pat. No. 5,195,984 to Schatz, issued on Mar. 23, 1993; U.S. Pat. No. 4,886,062 to Wiktor, issued Dec. 12, 1989; U.S. Pat. No. 4,655,771 to Wallsten, issued Apr. 7, 1987; U.S. Pat. No. 5443,500 to Sigwart, issued Aug. 22, 1995; and U.S. Pat. No. 4,580,568 to Gianturco, issued Apr. 8, 1986; which are all incorporated in their entireties herein by reference. The expanded inside diameter of the device may range from 3 to 20 mm, and the length of the device may range from 1 to 30 cm. The radially inwardly facing or radially outwardly facing sidewall of the stent may also be covered by a sheath as is known in the art. The sheath can be bonded to the surface of the stent so that the sheath remains in close apposition to the vessel wall.

Attached to the stent 14, a sensor 20 contains the sensing circuitry within its housing. Depending upon the stent 14 design and sensor 20 design, the attachment between the sensor 20 and the stent can take any of a variety of forms as will be apparent to those of skill in the art in view of the disclosure herein. For example, adjacent axially extending parallel struts of the stent design illustrated in FIG. 1A spread circumferentially apart upon expansion. Thus, the sensor 20 should be mounted to only colinear axial struts along the length of the stent unless the mounting is designed to accommodate circumferential separation of parallel struts. Alternatively, the sensor 20 may be positioned in an aperture which is cut in the sidewall of the stent 14, and attached to the strut portions adjacent to the edge of the aperture. Attachment may be accomplished in any of a variety of ways, such as by the use of adhesives, thermal bonding, soldering, welding or brazing, or mechanical interfit, depending upon the construction materials of the stent 14 and the sensor 20. Alternatively, the sensor 20 may be solvent bonded, adhesively bonded or otherwise attached to an expandable tubular sleeve which is positioned concentrically about the stent 14. Other attachment configurations can be devised by those of skill in the art in view of the disclosure herein.

In the illustrated embodiment, all or a portion of the sensor 20 is positioned on the radially outwardly facing surface of the tubular sidewall 18. Positioning the sensor 20 on the radially outwardly facing surface (sometimes referred to herein as the abluminal surface) may advantageously optimize blood flow through the central lumen 16 and/or reduce turbulence in the central lumen 16. Alternatively, the sensor 20 may be positioned on the radially inwardly facing surface (sometimes referred to herein as the luminal surface) of the stent. In addition, the stent struts or other elements which make up the sidewall 18 may be removed or modified at the portion of the sidewall corresponding to the sensor 20 such that the sensor 20 may be mounted within the resulting opening in the sidewall. Since the implantable sensor device 10, in accordance with the present invention, is preferably positioned within a healthy section of the vessel, the radial strength normally required for a stent in a post-angioplasty application is unnecessary. Thus, the present inventor believes that any reduction in radial support which may result from reasonably dimensioned apertures or other modifications to the sidewall to attach sensor 20 will not adversely affect the role of the stent as a sensor support structure in the context of the present invention. Additional details concerning the position of the sensor 20 with respect to the tubular wall 18 will be discussed below in connection with FIGS. 5A–5C.

The sensor circuitry 22 includes a sensing circuit 24, which is connected to a signal processing circuit 26, which is connected to a power source 28, a radio transmitter 30, and an antenna (not shown) to transmit signals about the glucose concentration to a remote device. The antenna (not shown) may be a thin wire wound around the stent 10. The power source 28 may be inductively coupled to an external device, or it may be a thin film rechargeable battery, as in Bates, J. B. et al., "*Thin Film Rechargeable Lithium Batteries for Implantable Devices*", ASAIO J., 1997 43:M644–M647, which is incorporated herein by reference.

The sensing circuit 24 is in electrical communication with a sensing surface (not illustrated in FIG. 1A) for sensing the analyte of interest in the fluid stream. In the embodiment illustrated in FIG. 1A, the sensor surface is preferably positioned radially inwardly from the radially inwardly facing surface of the tubular sidewall 18, to improve the useful life of the device as is discussed elsewhere herein. Thus, in an embodiment such as that illustrated in FIG. 1A in which the sensor 20 is positioned on the abluminal side of the tubular sidewall 18, the sensor surface is displaced radially inwardly such as by a radially inwardly extending portion of the housing or other support (not illustrated) to achieve the desired radial position of the sensor surface. Alternatively, in an embodiment in which the sensor 20 is positioned on the luminal side of the tubular side wall 18, or within or through an opening in the tubular sidewall 18, the sensor surface may be positioned directly on a radially inwardly-most extending portion of the sensor 20 as is discussed elsewhere herein.

The sensor surface is preferably covered by a semi-permeable membrane (not shown), which contacts passing blood when the stent 14 is placed in a blood vessel. The permeability of the membrane is selected to allow blood glucose, or the analyte of interest to freely contact the sensor, while restricting the passage of other blood components. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly (vinylidene fluoride) (PVDF), nafion or other biocompatible material. These membrane materials may also be used for the tubular sheath which can be used to surround either the luminal or abluminal surfaces of the stent. The membrane of the sheath may be bonded to the stent by adhesives or by tying (suturing) the two components together or by use of thermal bonding, soldering, welding or brazing, or mechanical interfit. The pore size of the lumenal membrane may be large enough to allow cells to come through if it covers the sensor surface, but the sensor membrane should have a pore size (MW cutoff of about 1000) which will allow glucose to pass, while restricting the passage of larger molecules. The entire tube surface does not have to be composed of the same membrane material. The part of the device near the sensing element can be composed of a different material or have a different porosity than the material in the rest of the device.

Referring to FIG. 1B, a remote circuit 32 is equipped with an antenna 34 and a signal processing unit 36, which converts the electronic signal from the embedded sensor into a concentration level or other indicium of the analyte. Preferably, an alarm circuit 38 and a display 40 are also provided. Information regarding the level of the analyte of interest can be displayed on the display 40 such as a monitor 42. The signal processing unit 36 may be provided with a lookup table or other baseline of normal or expected values for the analyte of interest. If the concentration of the analyte goes outside of the prescribed range, or if an electronic failure is detected, a warning audible, visible, or tactile signal is preferably produced from the alarm system 38. A transmitter 44 may also be included in the remote circuitry 32 in order to transmit data about the level of the analyte of interest to an implantable infusion pump, or the like.

The remote circuitry 32 can be provided in any of a variety of physical forms, depending upon the intended use of the device. For example, in a hospital or other immobilized patient setting, the remote circuitry 32 can be provided in a desktop or bedside housing and coupled directly to a display 40 such as a monitor 42. Alternatively, ambulatory patient devices may be provided by deleting a permanent coupling to the monitor 42 and packaging the remaining components of remote circuit 32 in a wearable form, such as a compact self-contained unit adapted for attachment to the wearer's clothing or including straps so that it can be strapped to the patient's body. In an ambulatory device, the signal processing unit 36 includes sufficient memory to record the glucose values over a predetermined period of time. The patient can couple the wearable device to an external monitor 42 or other electronics periodically, such as one or more times per day. Analyte data may thereafter be displayed in readable form, such as on a monitor 42 in table form or in graph form with a time unit on the X axis and a glucose value or derivative data on the Y axis.

The wearable unit (not illustrated) may additionally be provided with a data export coupling, such as a telephone connector, for connecting the signal processing unit 36 via internal or external modem into the telephone system. In this manner, the patient can transmit condensed analyte data to the healthcare provider for further monitoring and/or analysis. The wearable unit may additionally be provided with one or more manual data inputting elements ranging from a simple push button to a keypad, to allow manual data entry relating to significant dietary or other events. For example, meal times, significant fluid intake, manual insulin injection or other administration, or any of a variety of other significant events can be marked in the data, so that the patient or reviewing medical personnel can correlate the event with the blood glucose data.

Referring to FIG. 1C, there is schematically illustrated an implantable or externally wearable infusion pump 46. The infusion pump 46 may be controlled by the remote circuit 32 via a receiver 48 in the pump, or may be manually controlled using sensor information only as a guideline. The infusion pump 46 may be refilled through an appropriately designed port 50 such as a pierceable septum using a hypodermic needle or other appropriate delivery system. The infusion pump 46 may be implantable, as described by Irsigler et al., ("*Controlled Drug Delivery in the Treatment of Diabetes Mellitus*", Crit. Rev. Ther. Drug Carrier Syst. 1(3): 189–280 (1985)), which is incorporated herein by reference. Alternatively, it may be worn externally by the patient, and infuse insulin or other drugs as appropriate through a catheter 15 which is inserted into the patient's body. External insulin infusion pumps are currently marketed by suppliers like Medtronic, or Siemens. However, these pumps are not designed to receive a continuous signal from an implanted sensor, but instead are pre-programmed to approximate the patient's baseline insulin requirements. Such pumps can be modified with an with appropriate circuitry to receive and respond to output from the glucose sensor by those of skill in the art in view of the disclosure herein.

Figure 2:
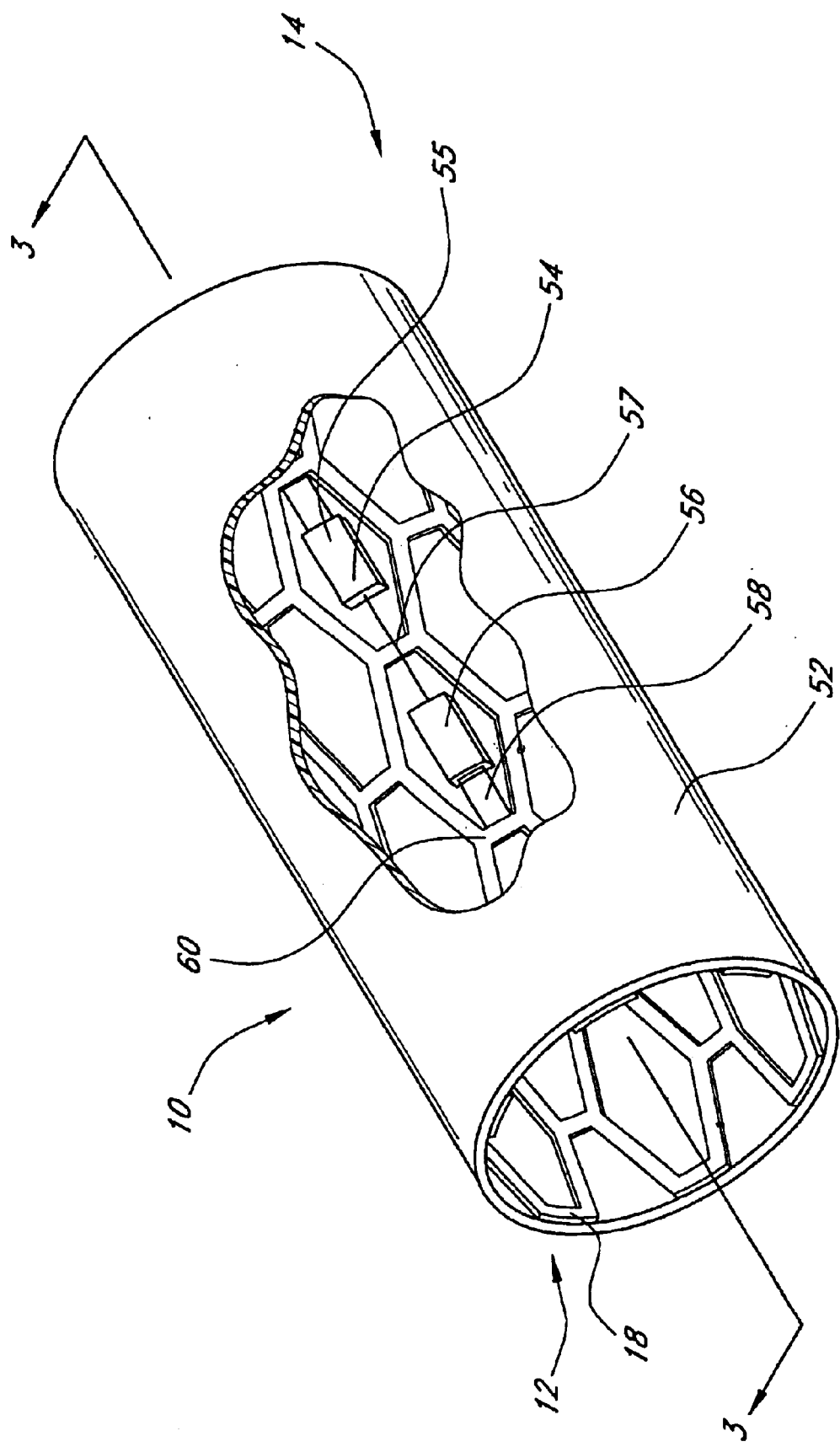
FIG. 2 is a perspective partial cut away view of a stent sensor device surrounded by a sheath.

Now referring to FIG. 2, a covered implantable sensor device 10 is shown. The sensor 10 comprises a cylindrical stent wall 18 surrounded by a sheath 52. An antenna (not shown) may be wound around the body of the sensor 10 and connected to the power source or the transmitter. All relevant electronics are schematically illustrated as in electronics housing 54 which is electrically coupled to a sensor 56 by one or more conductors 57. All such junctions of dissimilar metals are coated with polymers which are impermeable to bodily fluids in order to reduce galvanic corrosion. The analyte sensing element 56 is covered with a membrane 62 (FIG. 4) which is permeable to the analyte of interest. The analyte sensing element 56 extends radially inwardly within the sensor 10 where blood flow conditions are optimal.

Now referring to FIGS. 2, 4 and 5, the illustrated analyte sensing element 56 contains an enzyme gel layer 64, which is placed adjacent to the outer permeable membrane 62. The analyte diffuses through the membrane 62 to the gel enzyme layer 64. The reaction between the analyte and the enzyme occur in the gel enzyme layer 64. The reaction products then pass through an inner membrane 66 and react at the surface of a noble metal electrode 68, producing a current. An appropriate potential is applied to the electrode 68 from the power source contained in electronics housing 54 resulting in a signal, which is sent to the signal processing unit. The signal is then passed through the transmitter which transmits the information regarding the analyte of interest to an external monitor and/or implantable pump as has been discussed. The power source, the signal processing unit, and the transmitter are completely encapsulated in a housing 55 which is impermeable to biological fluids. The same housing 55 or a separate housing 70 also encapsulate the analyte sensor except for the membrane 62.

The sensor(s) to be incorporated into the device may be either electrochemical, piezoelectric, thermoelectric, acoustic, or optical. As known to those skilled in the art, there is a significant body of literature regarding the development of electrochemical glucose sensors. These generally incorporate an enzyme, which selectively reacts with glucose.

Electrochemical biosensors may be categorized as amperometric, conductometric, or potentiometric. Amperometric measurements are based on the oxidation or reduction or electrochemically active substances involved in the oxidation of glucose via glucose oxidase. Another method is measurement of changes in local pH due to the gluconic acid producing using a potentiometric sensor, usually a coated-wire pH selective electrode and/or ion-selective field effect transistor (ISFET). Conductometric sensors are based on the principle of electrical resistance changes during the reaction.

Potentiometric and conductometric sensors are currently limited due to the presence of numerous interfering chemicals in the environment. The main disadvantage of these sensors is their low sensitivity. The response of the potentiometric sensor depends on logarithmic changes in analyte concentration.

Microelectronics using ion selective field effect transistors (ISFET's) have been used for measurements of different analytes in body fluids (Erickson, K. A., et al., "Evaluation of a Novel Point-of-care System, the I-Stat Portable Clinical Analyzer", Clin. Chem. 39(2):283–287 (1993) which is herein incorporated). This allows miniaturization and integration of the transducer with associated electronic circuitry into a single chip. However, corrosion of the semiconductor material surface in saline and in physiological fluids is presently a problem for in vivo use. This problem may be corrected by surface coating or passivation of the ISFET. These types of sensors also belong to the class of potentiometric sensors, as described above.

Amperometric sensors respond linearly to the analyte concentration. If the limiting processes in signal generation are the enzymatic reactions, the dependence of the signal on glucose concentration is non-linear according to Michaelis-Menton kinetics. When the sensor operates in a glucose diffusion-limited mode, the signal is linearly proportional to the analyte concentration. Amperometric sensors are further subdivided into three classes:

1) Based on the production of hydrogen peroxide or consumption of oxygen.
2) Low molecular weight compounds used as mediators of the electron transfer process.
3) Direct electron transfer between the enzyme and the electrode.

Oxygen-electrode based sensors:

An operational enzyme electrode was first reported by Updike and Hicks (Updike, J. W., and Hicks, J. P., "*The Enzyme Electrode,*" Nature, 214: 986–8, (1967)) based on a description by Clark and Lyons (Clark L. C., and Lyons, C., "*Electrode Systems for Continuous Monitoring in Cardiovascular,*" Ann. NY Acad. Sci., 102:29–45 (1962)). In this process, the oxygen consumed in the oxidation of glucose is measured. The Clark oxygen electrode employs a platinum cathode held at a potential of approximately (–)0.6 V versus the saturated calomel electrode (S.C.E.), a sufficiently negative potential to reduce oxygen as follows:

$$O_2 + 4H^+ + 4e^- \rightarrow 2H_2O$$

Because the species being measured in this reaction is a gas, interference from other species in the biological fluid is negligible. However, the signal is determined from reduction of the initial current, making glucose determinations at low concentrations difficult. Further, the system requires the use of a second electrode without any glucose oxidase, to determine the local oxygen tension for the glucose measurement. In addition, it is necessary to insure that there is excess oxygen in the catalytic layer so that the reaction rate is limited by the glucose. The ratio of blood glucose to oxygen can be as high as 10 to 1 in arterial blood, and 100 to 1 in venous blood. (Jaffari 1995) An oxygen electrode sensor has been described by Armour et al. (1990), which was implanted in the superior vena cava of six dogs for up to 15 weeks, with good agreement with standard in vitro assays.

Hydrogen Peroxide based sensors measure hydrogen peroxide production based on the oxidation of glucose at potentials above +600 mV vs. SCE. This signal is directly related to the concentration of glucose in the sample.

$$H_2O_2 \rightarrow O_2 + 2H^+ + 2e^-$$

Unfortunately, the high operating potential required can also result in the oxidation of other chemical species in the blood. This may be overcome by the use of membranes. Bindra et al. (Bindra, D. S. et al., "*Design and in vitro studies of a needle type glucose sensor for subcutaneous monitoring*," Anal. Chem., 63: 1692–6 (1991)) reported glucose detection for up to 10 days in rats with a needle-type sensor, which consisted of GOD immobilized onto cellulose acetate as an inner membrane, and polyurethane as an outer membrane. Moussy et al. (Moussy, F. et al., "*Performance of subcutaneously implanted needle-type glucose sensors employing a novel trilayer coating*," Anal. Chem., 65: 2072–7 (1993)) used a needle type sensor with a trilayer coating. Nafion was used as an outer membrane, and poly (o-phenylenediamine) as an inner membrane to reduce interference from small electroactive species. GOD was immobilized between these two layers. As with the oxygen electrodes, the reaction must be limited by glucose, not oxygen.

In amperometric sensors with mediated electron transfer, oxygen as an electron acceptor is substituted by an artificial mediator, to overcome the tissue oxygen dependence of amperometric biosensors. Ferrocene and its derivatives are the most commonly used, although hexacyanoferrate (III), tetrathiafuvalene, and ruthenium hexamine (Jaffari, 1995) have also been investigated. In these sensors, a process involving the mediator instead of oxygen takes place:

$$GOD(red) + Mediator(ox) \rightarrow GOD(ox) + mediator(red)$$

At the electrode:

$$Mediator(red) \rightarrow Mediator(ox)$$

The electrochemical oxidation of the reduced mediator occurs at a low potential, thus reducing the sensitivity of the sensor to interfering compounds.

Limitations to the in vivo use of the sensor involve leaching of the mediator, and the possible toxicity of the mediator. This has been addressed by approaches such as:

1) Binding of the mediator to high molecular weight compounds,
2) Entrapment of the mediator and enzyme in conducting polymer films,
3) Covalent attachment of the mediator to a polymer film,
4) Modification of the enzyme with mediator molecules, and
5) Use of polymeric mediators.

All of these approaches have been investigated to reduce mediator leaching, although none have been tested in vivo (Jaffari, 1995).

An advantage of this type of sensor, since oxygen is not involved in the signal generation process, is that the sensor signal becomes independent of the oxygen concentration (Wilkins, 1996).

Amperometric sensors with direct electron transfer are independent of the oxygen concentration and involve direct oxidation of glucose by GOD at an electrode constructed from conducting organic salts (charge-transfer organic complexes with electron conductivity). Sensors based on this principle have been tested in vivo in rats, but little is presently known about the biocompatibility of such materials.

The most commonly used membrane for implantable biosensors is polyurethane (Jaffari, 1995). Other membranes which have been investigated include cellulose acetate, polypropylene, silicone rubber, and Nafion. These membranes have shown promise in short term monitoring, but long-term monitoring has been more difficult. Davies et al. (Davies, M. L., et al., "*Polymer membranes in clinical sensor application. Part 1: an overview of membrane function*," Biomaterials, 13: 971–89, (1992)) have reviewed extensively the range of polymers used as membranes for biosensors. Updike reported that immobilization of glucose oxidase within a membrane allowed it to accurately measure glucose levels for well over one year.

In a preferred embodiment, an amperometric electrode is used. The characteristics of such an electrode, such as one available from Minimed, Inc. (Sylmar, Calif.), is related to the production of hydrogen peroxide in the conversion of glucose to gluconic acid by glucose oxidase. The noble metal electrode 68 may be connected to any of a variety of RF transceivers. To avoid the use of batteries, which may be too large for this application, the system may be powered by, and signal transmission occurs via an inductive link. This requires an inductive coil (not shown) to be placed both inside the external receiver and an inductive coil (not shown) within the implantable sensor device 10. An example of the type of transceiver to be used is employed in the Ventak Mini IV automatic implantable cardioverter defibrillator (Guidant Corp, Santa Clara, Calif.). The transceiver coil in the preferred embodiment is specifically adapted for use with a stent platform. The size of the coil, in addition to the number of turns around the implant limits the power and signal transmission distance between the implant and the external receiver/power supply. In order to maximize the diameter of the coil, the coil is wound around the outside of the implantable sensor device 10. The transceiver coil is made from an electrically conductive material, and is coated to prevent corrosion. The coil may be aligned with and bonded to the struts of the implantable sensor device 10, in order to minimize any impact on expansion of the implantable sensor device 10. Alternatively, the struts of the implantable sensor device 10 themselves may serve as the antenna coil. In addition, in order to maximize signal transmission, the internal and external coils should be aligned so that their major axes are parallel. The external receiver coil should contain a ferrite core to optimize power and signal transmission. The external receiver and power supply should be designed so that it can be worn on the patient's body, and can be oriented to maximize the signal from the implanted sensor. This can be done by custom-placed foam padding to orient the external receiver and power supply.

Figure 6A:
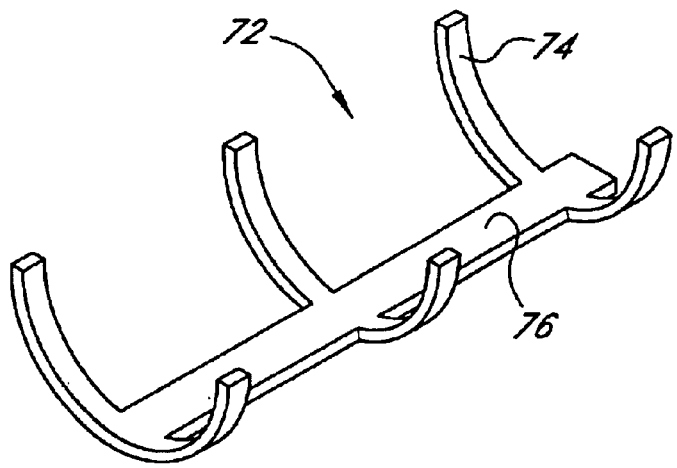
FIG. 6A is a perspective view of an alternate support structure in accordance with the present invention.
Figure 6B:
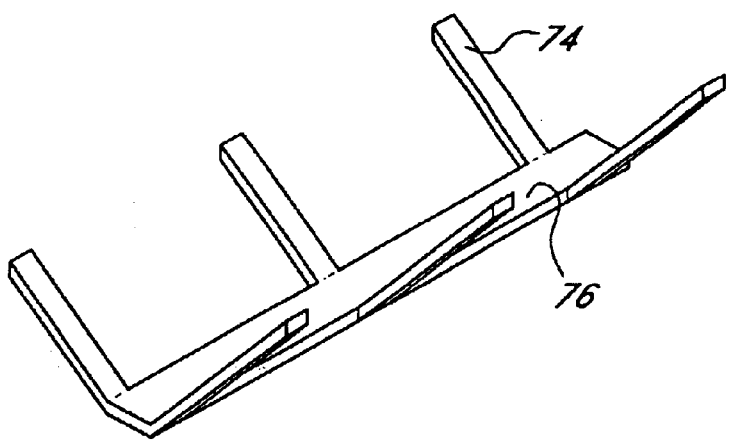
FIG. 6B is a perspective view of a further support structure in accordance with the present invention.
Figure 6C:
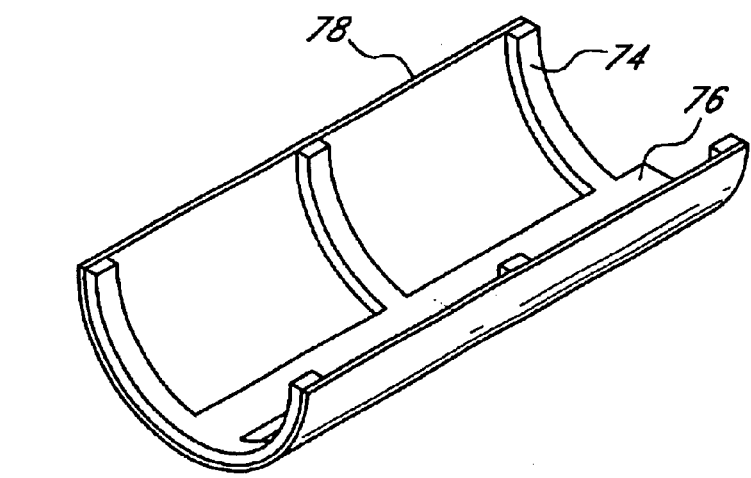
FIG. 6C is a perspective view of the support structure illustrated in FIG. 6A, provided with an outer fabric sheath.

Now referring to FIGS. 6A–6C, alternatively, the sensor device may be held in place within the vessel by any of a variety of anchoring systems other than a graft or stent. For example, any of a variety of anchoring structures may be provided with hooks or barbs to engage the vessel wall. Alternatively, semicircular cages or struts may be used, which only extend through a partial circumference of the vessel. FIG. 6A shows struts 74 that can be positioned securely against a blood vessel. An axially extending strut 76 connects the circumferential struts 74, and also could support a sensor. The support 72 can be manufactured in a variety of ways, such as by injection molding a suitable polymeric material or by laser cutting from stainless steel, Nitinol or other tube stock. FIG. 6B shows alternate struts 74 that can be secured against the vessel wall. Again, connecting struts 74 is one or more connecting struts 76. FIG. 6C shows a modification of the device shown in FIG. 6A, where the support 72 is provided with a sheath 180.

In order to implant an implantable sensor device within the vasculature of the patient, a catheter-based delivery system is used. All implantable sensor devices are formed to include a central lumen with a diameter in the reduced profile sufficient to allow passage of a guide wire and a catheter tip through it. The implantable sensor device is mounted onto a catheter tip, and then collapsed to as small a diameter as possible. The implantable sensor device may be deployed by removal of a deployment sheath, or other methods, which may be preferred for the specific type of stent platform being employed. These methods are well known in the art. After the implantable sensor device is deployed, the catheter and guidewire are removed from the (now enlarged) central lumen in the implantable sensor device. The implantable sensor device is placed such that neither the catheter nor the guidewire adversely affects the electronic circuitry.

Preferably, the implantable sensor device is implanted in a relatively large artery or vein (>5 mm) in order to minimize the risk that the implant may occlude the artery. In addition, a healthy artery or vein should be chosen, so that the device can open completely, and so that the flow patterns are normal.

Clinically, it is now accepted practice to place the stent in a parent vessel so that the stent struts cross the ostium of a side branch vessel. This is called "stent jail." (Pan, M., et al., "*Simple and Complex Stent Strategies for Bifurcated Coronary Arterial Stenosis Involving the Side Branch Origin*," Am. J. Cardiol., 83: 1320–25 (1999)). In addition, for stent-grafts for aortic aneurysm repair, investigation is being carried out regarding stent struts which cross the renal artery ostia. An example of such a suprarenal device is the Talent Aortic Stent-Graft (Medtronic, Inc.). This suggests that it is possible to have a wire (or transducer) which is placed directly across an artery without thrombus formation or thrombo-embolization. Thus, in an alternative embodiment, the sensor or sensing element (i.e., the transducer) can be placed directly across the path of the flowing blood, on a surface with low cross-sectional area, such as a wire with a diameter of 0.003" to 0.025", or a ribbon, oriented with its narrow edge facing upstream. The transducer or sensor can be placed on either the proximal, distal, or lateral faces of the wire or ribbon.

As with sensors mounted on or near the wall of the vessel, it is important that the sensor be placed across a large vessel with high blood velocity. This will not result in significant thrombus deposition, and any emboli which may result will be of sufficiently small size that they will be readily lysed by the patient.

As with stents, there are a multitude of possible designs for a sensing element which is placed directly across the bloodstream, as will be appreciated by those skilled in the art. The transducer (or sensing element) could be placed along the surface of a single, straight wire. FIG. 9A shows a cross-sectional view through a stent 14, which includes a sensing element 120 consisting of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is either part of or is bonded to the stent 14. The shape memory material allows the electrode 68 and sensing element 120 to be positioned directly across the lumen of the vessel, as described above. The electrode 68 is connected to the signal processing unit (not shown) through a conductor (not shown). The remainder of the implantable sensor 10, including the power source, signal processing unit, transmitter, and stent, are positioned to be flush against the vessel wall.

FIG. 9B shows an implantable sensor device 10 with a sensing element 130 across the cross-section of the stent 14, with sensor circuitry 22. FIG. 9C shows an enlarged cross-sectional view of the sensing element 130 of FIG. 9B, taken along the 9C—9C line. The sensing element 130 consists of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is bonded to the stent 14 on both ends. The sensing element 130 is connected to the sensing circuit 24 through a conductor (not shown).

FIG. 9D illustrates a transducer 140, consisting of a wire-like noble electrode 68, which in turn is covered by a gel-enzyme layer 64 and finally by an analyte-permeable membrane 62, which is bound to a wire-like structure made of a shape memory material 110 such as nitinol, which is bonded to the stent 14. The sensing element 140 is connected to the sensing circuit 24 through a conductor (not shown).

FIG. 9E shows another configuration with quadruple sensing elements 150, each at right angles to each other, attached to stent 14, with sensor circuitry 22. The sensing elements 150 are connected to the sensing circuit 24 through a conductor (not shown). Alternatively, multiple transducers could be positioned to form a wire mesh, provided the mesh size is sufficiently large to permit blood flow without significant thrombo-embolization. In other acceptable configurations, a very small sensor surface area impedes blood flow, compared to the blood vessel's cross-sectional area.

Referring to FIG. 7A, there is disclosed a deployment catheter 80 which may be utilized to deploy a self-expandable stent type sensor support in accordance with the present invention. The catheter 80 comprises a proximal end 82, a distal end 84 and an elongate flexible tubular body 86 extending therebetween. The length of the tubular body 86 will vary depending upon the intended access point and deployment site for the stent sensor. For example, lengths in the area of about 120 cm to about 140 cm are typical for use in a coronary artery implantation by way of a femoral artery percutaneous puncture site. Other lengths for different access sites and deployment sites will be apparent to those of skill in the art in view of the disclosure herein.

The tubular body 86 may be manufactured in accordance with any of a variety of known techniques, such as by extrusion of appropriate biocompatible polymeric materials. Known materials which are commonly used for this application include high density polyethylene, polytetrofluroethylene, nylons, and a variety of others known in the art. Alternatively, at least a portion or all of the lengths of the tubular body 86 may comprise a spring coil, solid wall hypodermic needle tubing, or braided reinforced wall, depending upon the functional requirements of the catheter.

For most applications, the tubular body 86 will be provided with an approximately circular cross-sectional configuration having an external diameter within the range of from about 0.025 inches to about 0.065 inches. In accordance with one embodiment of the invention, the tubular body 86 comprises a multilumen extrusion having an external diameter of about 0.042 inches (3.2 f) throughout substantially all of its length. Alternatively, the tubular body 86 can have diameters as large as 12 Fr or higher. For percutaneous placement into larger vessels such as the iliac artery. Additional dimensions, materials and manufacturing techniques are well known in the angioplasty catheter art.

The proximal end 82 is provided with a manifold 88, having a variety of access ports depending upon the desired functionality of the catheter 80. In the illustrated embodiment, the manifold 88 is provided with a guidewire port 90 and a deployment wire port 94. Manifold 88 may be manufactured by injection molding, or other techniques known in the art.

The distal end 84 of deployment catheter 80 is provided with a collapsed support structure 96 having a sensor housing 20 thereon in accordance with the present invention. The support structure 96 is illustrated in its collapsed, low profile configuration, such as for transluminal advancement towards a placement site. The tubular body 86 may be provided with an annular recess 98 near the distal end 84, for receiving the support structure 96. In addition, the tubular body 86 may be provided with a recess for receiving the sensor housing 20, thereby reducing the collapsed profile of the loaded catheter 80.

The support structure 96 may be constrained in its reduced crossing profile configuration in any of a variety of ways as has been discussed. In this illustrated embodiment, the support structure 96 is restrained in its collapsed configuration by a deployment wire 94. Deployment wire 94 extends throughout the length of the tubular body 86 through a deployment wire lumen 108, such that a proximal end of the deployment wire 94 may be proximally retracted by the clinician. The distal end of the deployment wire 100 exits the tubular body 86 at a deployment wire port 100, and loops the support structure 96 in one or more loops or slip knots 102 to restrain the support structure 96 in its collapsed configuration. Loops or slip knots 102 are configured such that proximal retraction on deployment wire 94 causes the loops or slip knots 102 to become untied or otherwise disengaged, thereby releasing the support structure 96 so that it expands radially outwardly from its low profile introduction configuration to its radially enlarged implanted configuration. For applications in which the deployment site is removed from the percutaneous access site, the catheter 80 is preferably introduced over a guidewire as is known in the art. For this purpose, a distal guidewire opening 104 is in communication with the proximal guidewire port 90 by a guidewire lumen 106 extending therebetween.

An example of a similar delivery system is shown in U.S. Pat. No. 5,873,906 to Lau, et al. issued Feb. 23, 1999, which is herein incorporated by reference.

Figure 7B:
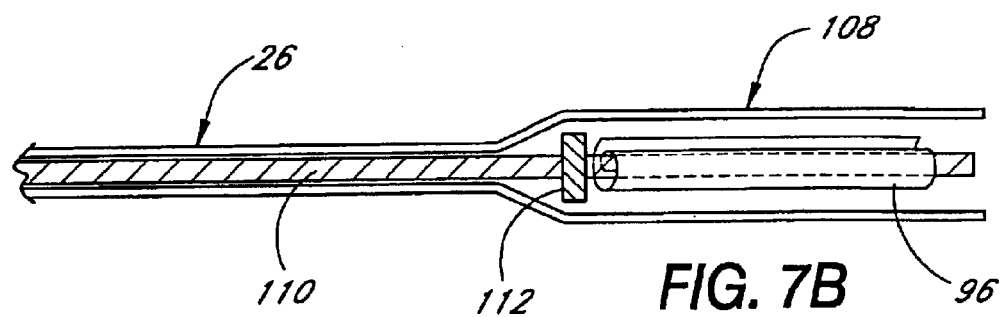
FIG. 7B is a cross-sectional view of a catheter-based delivery system for a rolled sheet type self-expanding stent with an embedded sensor.

Referring to FIG. 7B, the self-expanding implantable sensor device 96 can be deployed from a tubular restraining sheath 108 by pushing a rod 110 optionally attached to a disk 112, until the implantable sensor device 96 is pushed clear of the restraining sheath 108. An example of such a technique is described in U.S. Pat. No. 5,411,551 to Winston et al. (issued May 2, 1995).

Figure 7C:
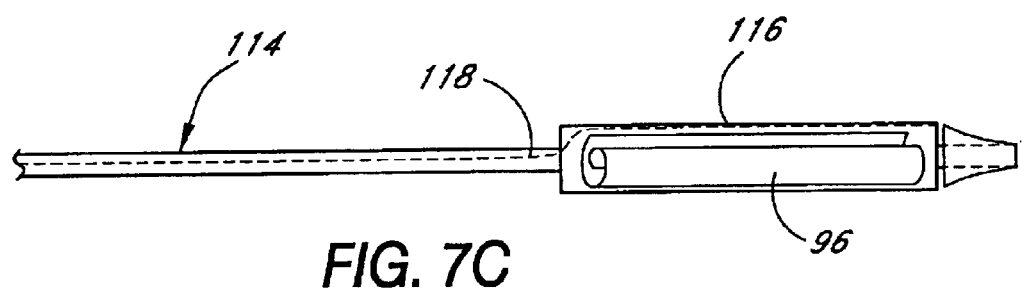
FIG. 7C is a cross-sectional view of a catheter-based delivery system, which uses a restraining sheath, for a self-expanding stent with an embedded sensor.

Referring to FIG. 7C, another deployment method for a self-expanding implantable sensor device 96 is shown. The implantable sensor device 96 is restrained onto the shaft of the catheter 114 by a sheath 116 and a tether line 118. The sheath 116 unfolds when the tether line 118 is pulled, allowing the implantable sensor device 96 to deploy.

Figure 7D:
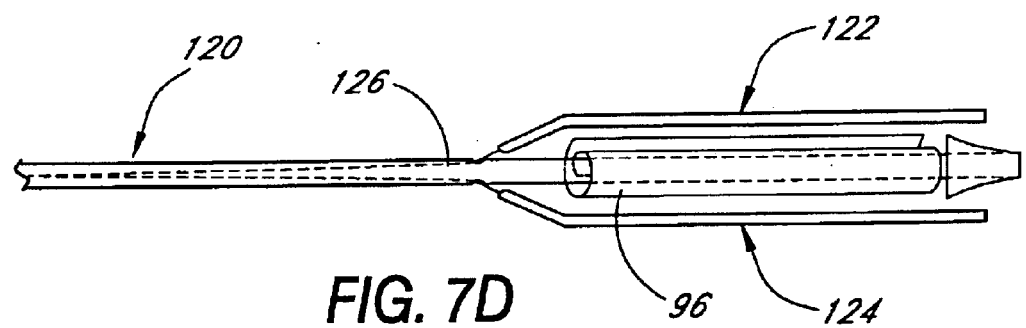
FIG. 7D is a cross-sectional view of a catheter-based delivery system, with a pull-away sheath, for a self-expanding stent with an embedded sensor.

Now referring to FIG. 7D, another deployment method for a self-expanding implantable sensor device 96 is shown. The implantable sensor device 96 is restrained onto the shaft of the catheter 120 by two or three or more restraining prongs 122,124. The restraining prongs 122,124 are retracted when one or more deployment wires 126 are pulled, allowing the implantable sensor device 96 to expand. An example of this can be shown in U.S. Pat. No. 6,024,763 to Lenker et al. (issued Feb. 15, 2000), which is herein incorporated by reference. However, in this patent, the rails are only designed to minimize frictional forces between a deployment sheath and the device. They are not actually used as the deployment mechanism. In the present case, prongs can be used to minimize the delivery profile of the device. Since the sensor and electronic circuitry may not collapse to a profile as small or as circular as a stent or stent-graft, it may be more appropriate to position the electronic components on one side of the catheter, and layer the collapsed stent on the opposite side of the catheter. This could be achieved by use of delivery prongs, as described.

Figure 7E:
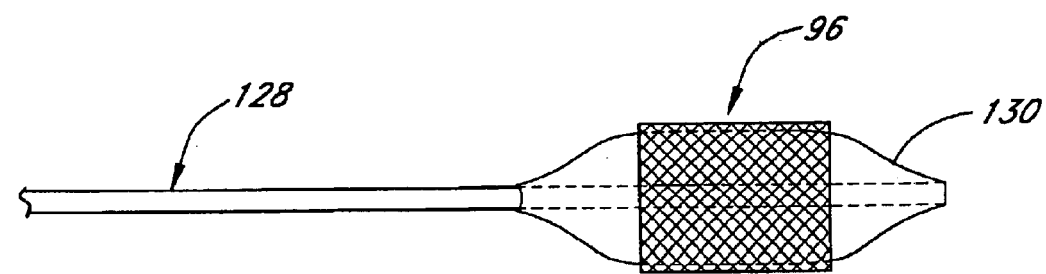
FIG. 7E is a cross-sectional view of a catheter-based delivery system for a balloon expandable stent with an embedded sensor.

Referring to FIG. 7E, the implantable sensor device 96 may be deployed by use of a suitable balloon catheter 128 if a balloon expandable stent platform is used. The balloon 130 is inflated at elevated pressures of 2 to 20 atmospheres, and after the implantable sensor device 96 is fully expanded, the balloon 130 is deflated and then the balloon catheter 128 is withdrawn. Use of such balloon catheters is well known in the art.

Figure 7F:
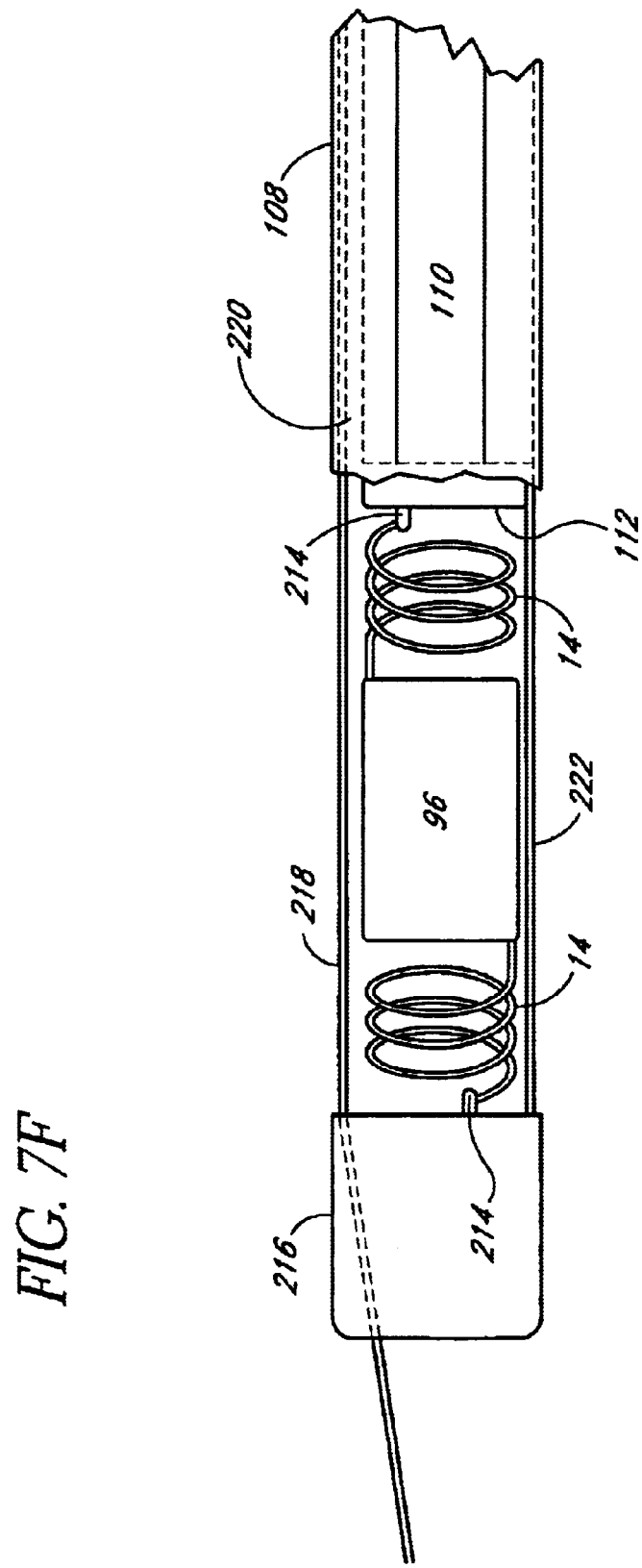
FIG. 7F is a cross-sectional view of a catheter-based delivery system for a self-expanding stent with an embedded sensor, in which the guidewire lumen passes on either side of the sensor.

Referring to FIG. 7F, the self-expanding implantable sensor device 96 can be deployed from a tubular restraining sheath 108 by proximally retracting the sheath 108 with respect to a push rod 110 optionally attached to a disk 112, until the implantable sensor device 96 is exposed clear of the restraining sheath 108. The constrained stent support structures 14 at either end of the sensor 96, may be held in place by a release mechanism, 214, which may be a simple knob or hook. Prior to deployment, the atraumatic catheter tip 216 is in direct apposition to tubular restraining sheath 108. As the sensor device is pushed clear of the restraining sheath, a small shaft 222 connects the push rod 110 or disk 112 to the catheter tip 216. A guidewire 218 passes through guidewire lumen 220, which may be located eccentrically with respect to the axis of the catheter. An example of a similar technique is described in U.S. Pat. No. 5,411,551 to Winston et al. (issued May 2, 1995) which is incorporated herein by reference. However, in Winston, the guidewire passes directly through the center of the catheter, whereas in the present disclosure the guidewire passes eccentrically through the delivery catheter. Allowing the guidewire to pass eccentrically through the catheter allows the sensor to be hermetically sealed, and permits a less complex sensor geometry. Additionally, the eccentric guidewire lumen provides a smaller delivery profile for the sensor and its delivery system.

Figure 5C:
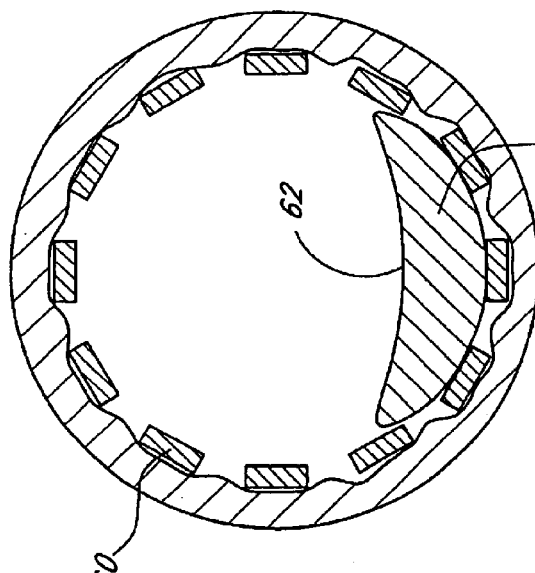
FIG. 5C is a cross-sectional view as in FIG. 5A of a stent with an embedded sensor mounted completely on the luminal side of the stent.
Figure 5B:
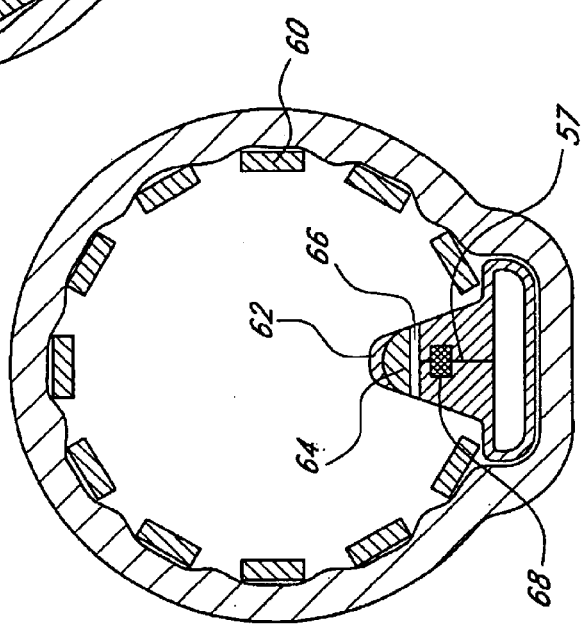
FIG. 5B is a cross-sectional view as in FIG. 5A of a stent with an alternate configuration for the embedded sensor.
Figure 5A:
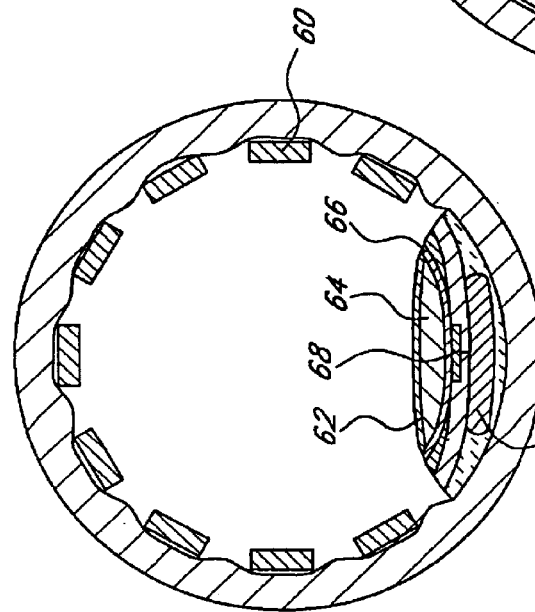
FIG. 5A is a cross-sectional view through a stent showing one mounting configuration of an embedded sensor in accordance with one embodiment of the present invention.

Now referring generally to FIGS. 5A–C, as the blood passes over the sensor 20, glucose diffuses through the semi-permeable membrane 62. The housing design should keep the blood shear rate at the apex of the housing sufficiently high that there is minimal thrombosis on this surface and any formed thrombus will be of minimal thickness. Thus, diffusion of glucose through the semi-permeable membrane 62 should be the rate-limiting step, and surface of the device should not become covered in a fibrous capsule, as in the case of subcutaneous sensors. The glucose reacts with the glucose oxidase to produce hydrogen peroxide, which further reacts to produce an amperometric signal. The amperometric signal is converted by an appropriately designed electronic circuit so that it may be transmitted using the RF transceiver.

In general, the surface of the sensor 20 should be placed on the luminal side of the stent. With the exception of the glucose permeable membrane, which is part of the sensor, the electronic components of the sensor should be encapsulated in a conformal coating such as a fluoropolymer or a polyamide, and injection-molded or dip-coated in a silicon rubber, polyurethane, or other biocompatible housing material.

The sensor housing should be given a streamlined shape, with gradually sloped transitions at both its proximal and distal ends, in order to minimize flow disturbances. The housing should be as wide or wider at its base than at its apex. The apex of the housing should not protrude higher than 5–50% of the diameter of the fully deployed device. The glucose permeable membrane 62 should be placed at the apex of the housing, should not be encapsulated in the housing material, and should face the bloodstream. The glucose permeable membrane 62 should occupy the majority of the area of the housing apex.

Alternatively, if the device includes a graft on the luminal surface of the stent, the sensor may be placed on either the luminal or abluminal surface of a graft material. If the graft is place on the abluminal surface of the stent, the sensor should be placed on the luminal surface of the graft. The graft material is preferably a fluoropolymer, such as ePTFE. If the housing is placed on the luminal surface of the graft, it is bonded by partially dissolving the housing material thermally or using an appropriate solvent so that the housing becomes physically interpenetrated with the graft or with an appropriate adhesive, such as melt-processed poly (tetrafluoroethylene-co-hexafluoropropylene) (FEP). If the sensor is placed between the stent structure and the graft, it should be bonded to both the stent and the graft, to prevent graft movements from causing thrombosis.

Generally, the height of the sensor is estimated to be 2 to 3 times the thickness of a stent strut, based on some observations of a limited number of stent designs (Virmani, 1999). This estimate represents the approximate thickness of the fibrous tissue layer above the stent surface. Thus, the sensor height above the stent luminal surface should be 1–2 times the thickness of a stent strut. The strut thickness varies with design, but is roughly 0.005" to 0.010" (0.13 to 0.26 mm). Thus, by using this approach, the housing should protrude about 0.2 to 0.5 mm above the stent luminal surface.

The effect that this will have on the target vessel is a function of the diameter of the vessel, as given in the following table:

| Vessel Diameter (mm) | Sensor Height above struts (mm) | Loss in Diameter (%) | Loss in Area (%) |
| --- | --- | --- | --- |
| 10 | 0.5 | 5.0 | 9.8 |
| 10 | 0.2 | 2.0 | 4.0 |
| 9 | 0.5 | 5.6 | 10.8 |
| 9 | 0.2 | 2.2 | 4.4 |
| 8 | 0.5 | 6.3 | 12.1 |
| 8 | 0.2 | 2.5 | 4.9 |
| 7 | 0.5 | 7.1 | 13.8 |
| 7 | 0.2 | 2.9 | 5.6 |
| 6 | 0.5 | 8.3 | 16.0 |
| 6 | 0.2 | 3.3 | 6.6 |
| 5 | 0.5 | 10.0 | 19.0 |
| 5 | 0.2 | 4.0 | 7.8 |

As is evident from the table, the smaller the vessel and the greater the sensor height, the greater the obstruction which is created. Design requirements will vary and require investigation for each application as is well known in the art.

This table also provides insights into the intrusion of the sensor as a percentage of post-deployment vessel diameter. A native vessel with greater than 50% diameter stenosis is clinically defined to be a restenotic vessel, and typically requires re-intervention It is estimated that the sensor should not obstruct more than about 25% of the vessel diameter. Alternatively, the percent area loss of a vessel, along with a sensor height, cab be examined and examples are tabulated below:

| Vessel Diameter (mm) | Sensor Height above struts (mm) | Loss in Diameter (%) | Loss in Area (%) |
| --- | --- | --- | --- |
| 10 | 0.5 | 5.0 | 9.8% |
| 10 | 2.5 | 25.0 | 43.8% |
| 9 | 0.5 | 5.0 | 9.8% |
| 9 | 2.3 | 25.0 | 43.8% |
| 8 | 0.4 | 5.0 | 9.8% |
| 8 | 2.0 | 25.0 | 43.8% |
| 7 | 0.4 | 5.0 | 9.8% |
| 7 | 1.8 | 25.0 | 43.8% |
| 6 | 0.3 | 5.0 | 9.8% |
| 6 | 1.5 | 25.0 | 43.8% |
| 5 | 0.3 | 5.0 | 9.8% |
| 5 | 1.3 | 25.0 | 43.8% |

Using this approach, the sensor height can range from about 0.3 to 2.5 mm in height above the stent luminal surface.

With regard to flow velocity, flow measurements in piping systems are commonly obtained from the pressure drop across a restriction, such as a Venturi meter. As is discussed above, the restriction should not be greater than about 25% of the vessel diameter. Since the volumetric flowrate, Q, must be the same both proximal to and within the restriction, the velocity within the restriction is related to the upstream velocity by:

$$v_2 = v_1(A_1/A_2)$$

Therefore, for an approximately 25% restriction in diameter, the restriction in area is about 43.8%, and the velocity within the restriction is about 178% of the upstream velocity, and for an approximately 5% restriction in diameter, the velocity within the restriction is approximately 111% of the upstream velocity.

The above analysis is true for situations where the velocity profile is almost flat, e.g., in turbulent flow in a pipe. For laminar flow, there will be a parabolic velocity distribution, with zero velocity at the wall, and maximum velocity occurring in the middle. This distribution may be somewhat impractical to measure, so the exact position where 178% of the proximal velocity occurs may be hard to establish. Thus, another approach to determining the proper height of the sensor is to find the sensor height where the blood velocity is approximately 125–200% of its proximal velocity. This can be determined using duplex ultrasound, or hot-wire anemometry, or other flow-measuring techniques. Using this approach, the sensor may be flush mounted against the wall of the vessel, with a flow impedance device mounted at the same axial position within the vessel, in order to increase the velocity within the sensor/impedance device to about 125–200% of the proximal flow velocity. The location where the estimate of the proximal flow velocity is approximately 200% is preferred. This would allow for the possibility of flush mounted sensors.

One key problem with most implanted sensors is fibrous tissue encapsulation. While proper positioning of the sensor within the vessel can minimize the thickness of a fibrous tissue layer, it may not be possible to avoid endothelialization of the sensor surface. Thus, the sensor design of the current invention may not actually project completely beyond the tissue growth, but the thickness of the tissue layer would ideally be only a single layer of endothelial cells.

Prior to implantation, the sensor may be checked for a linear response to glucose concentration. This may be done in the operating theater using sterile technique immediately prior to implantation, or may be done in a batch-wise manner during the manufacturing process. Following implantation, the sensor may then be calibrated by comparison of the output signal with an accepted standard. Typically, this may be done by comparing the signal with the value obtained from a laboratory glucose sensor, such as made by Yellow Springs Instruments (Yellow Springs, Ohio). Preferably, the calibration curve should be stable over time and for wide range of glucose values. For example, the slope of the calibration curve should be sufficiently stable to give an error of less than ten percent. Weekly calibrations should be sufficient to insure stable and accurate readings, however calibration can be performed as frequently as required. For example, there may be a change in sensitivity over the first month or so, if the transducer becomes endothelialized. However, after that point, the system should be stable. Thus, calibrations could be required as often as every other day at first, and taper off to no more than about once per week.

Once calibrated, if the external signal produced by the sensor indicates that the glucose level is outside of the normal physiological range, there are several possible outcomes.

1. An audible, visible or tactile alarm may sound, so that the patient or physician may check the sensor with a home glucose monitoring kit (e.g., One Touch, LifeScan, Johnson & Johnson), and then take appropriate action such as administration of insulin or glucose.

2. The signal may be transmitted directly to an implantable insulin pump, which may administer insulin directly without requiring a response by the patient.

FIGS. 5A–C show various embodiments in which the sensor and transmitter are on either the luminal or abluminal surface of the stent. Now referring to FIG. 5A, an implanted sensor 20 is shown in a transverse cross-sectional view through the vessel. The struts 60 of the implantable sensor device may be surrounded by an inner tubular sheath (not illustrated for simplicity), which would contact the blood vessel wall when deployed. The sensor housing 20 sits between a pair of struts 60. The membrane 62 is exposed to the blood flow. The analyte sensor 56 will normally have a larger cross-sectional area than the stent struts 60. The outer sheath allows for enhanced uniform radial expansion (beyond that of self-expanding struts), especially if the sheath is bonded to each of the struts 60 of the stent, and is bonded through the length of the stent, not just at the ends. This would link each of the struts 60 to its neighbors, preventing uneven expansion. It would also be advantageous to make the sheath out of a material which could be stretched slightly to obtain its final diameter, so that irregularities in the flow surface are minimized, except in the region of the sensor.

When a non-sheath implantable sensor device is either balloon expanded (or in the case of self-expanding stents, following balloon touch-up), the stent struts 60 can be embedded more deeply into the vessel wall than the sensor housing 20. If the struts 60 were positioned between the flowing blood and the sensor surface, they would cause flow stagnation, and therefore thrombosis on the membrane 62 of the sensor. If the sensor is placed instead on the luminal surface of the stent, the sensor will again be embedded less deeply in the vessel wall, although without struts 60 on its luminal surface, there will be minimal hemostasis and thrombus formation on the transducer surface.

As it can be seen, the sensor could be placed either between the stent struts and the inner sheath, or on the luminal surface of the inner sheath. In both cases, a semipermeable membrane might still be necessary to insure that only the analyte of interest reaches the surface of the sensor. In either case, the sensor should be designed with a streamlined profile at both its proximal and distal ends, to minimize regions of hemostasis.

In accordance with another aspect of the invention, the sensor and its associated circuitry are connected between two or more stent segments, with or without the presence of a stent or supporting member at the location of the sensor. This provides a number of advantages, including a decrease in the delivery profile, and an increase in flexibility. This allows easier access to sites with tortuous vascular anatomy, but will still allow the sensor to maintain its same relative position in the blood vessel.

Figure 10:
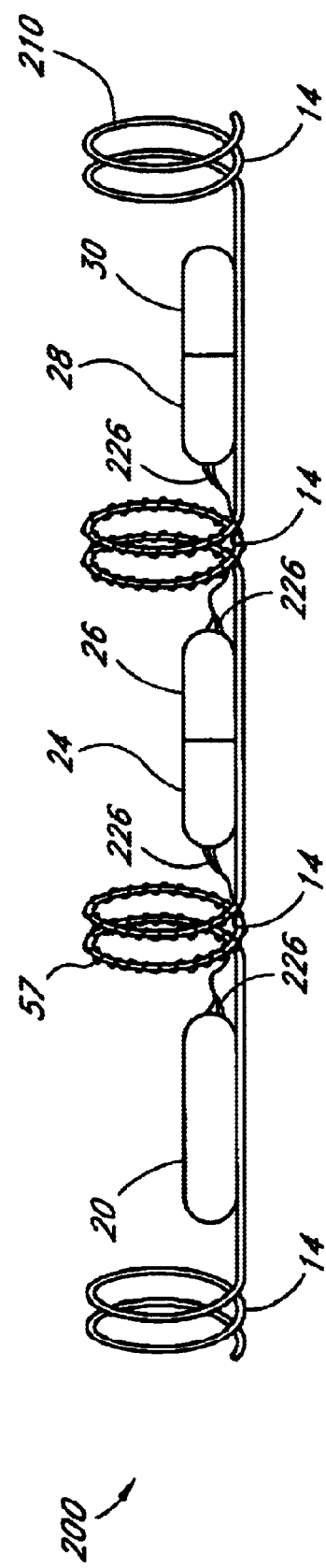
FIG. 10 shows a side elevational view of a sensor and transmitter, with expanded anchoring stents at the proximal end of the sensor, intermediate between the sensor and transmitter, and at the distal end of the transmitter.

FIG. 10 shows a side elevational view of a sensor 20, a sensing circuit 24 and signal processing unit 26, a power source 28 and a radio-transmitter 30, with expanded anchoring stents 14 at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. Each segment of the implantable sensor device is connected to its neighboring segment by the use of electrical connectors 57, with strain relief elements 226. The electrical connectors 57 are hermetically sealed. Additionally, the electrical connectors 57 are of sufficient length, and have redundancies so that they can connect the various segments allowing flexibility of positioning between each segment of the implantable sensor while minimizing the strain imparted on the connectors. It is important to note that the relative position of each of these components between the anchoring stents is somewhat arbitrary. The device could be designed with these components in any order, and still function equally well, as will be apparent to those skilled in the art.

FIG. 11 shows a side elevational view of a sensor 20, a sensing circuit 24 and signal processing unit 26, a power source 28 and a radio-transmitter 30, with anchoring stents 14 in the compressed state such as within a tubular deployment catheter at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. The advantages of this segmented embodiment of the invention are that the overall delivery profile of the device is reduced, and the device becomes more flexible for delivery through tortuous vessels.

Thus, the present invention provides at least one electrical component, having at least a first support on a proximal end and a second support on a distal end, for supporting the component in a body lumen. As disclosed herein, the electrical circuitry may desirably be divided into at least two or three discrete physical components spaced axially apart and in electrical communication with each other to minimize the implanted profile and enhance deliverability. Each of the components may be provided with a proximal and a distal support, as illustrated in FIGS. 10 and 11. The two or three or four or more supports may be connected together independently of the intervening electrical component, or may be connected only through the housing of the intervening electrical component. The supports may comprise any of a variety of self-expandable coils or other structures well known in the self expandable stent and graft (e.g., abdominal aortic aneurysm graft) arts. Alternatively, balloon expandable or mechanically expandable anchor structures may be used. In an alternate configuration, the support may comprise an elongated ribbon or wire such as Nitinol which is based into a spiral, having the electrical components spaced axially apart therealong.

Although the present invention has been described in connection with certain preferred embodiments, persons of ordinary skill in the art will understand that many modifications can be made thereto within the scope of the claims which follow. Accordingly, the scope of the invention is not intended to be limited by the above description but instead is to be determined entirely by reference to the following claims.

What is claimed is:

1. An implantable sensor for sensing the presence of an analyte in a vessel, comprising:
    at least two substantially tubular support structures directly connected to one another, for anchoring the sensor in the vessel, each support structure having a side wall with a luminal side facing toward the center of the vessel and an abluminal side facing toward the wall of the vessel;
    a sensor housing carried by the support structures, the housing having a streamlined exterior configuration to minimize blood flow turbulence and located between two support structures;
    a power supply and electrical circuitry in the housing; and
    a sensing surface exposed to the exterior of the housing;
    wherein the sensing surface is positioned on the radially inwardly most portion of the luminal side of the housing.

2. An implantable sensor as in claim 1, wherein the sensor housing is positioned on the luminal side of the support structures.

3. An implantable sensor as in claim 1, further comprising tubular sleeves surrounding the tubular support structures.

4. An implantable sensor as in claim 3, wherein the tubular sleeves are on the abluminal surface of the tubular support structures.

5. An implantable sensor as in claim 3, wherein the tubular sleeves are on the luminal surface of the tubular support structures.

6. An implantable sensor as in claim 3, wherein the tubular sleeves comprise ePTFE.

7. An implantable sensor as in claim 1, further comprising an analyte permeable membrane and an enzyme gel layer.

8. An implantable sensor as in claim 7, wherein the enzyme gel layer comprises glucose oxidase.

9. An implantable sensor as in claim 1, wherein the sensor comprises an amperometric sensor.

10. An implantable sensor as in claim 1, wherein the sensor comprises an electrode selected from the group consisting of oxygen electrodes, hydrogen peroxide electrodes, and electrodes with mediated electron transfer.

11. An implantable sensor as in claim 1, wherein the sensing surface is spaced radially inwardly from the luminal side by a distance of at least about 0.2 mm, such that the velocity of blood in the vessel inhibits obstruction of the sensing surface.

12. An implantable sensor as in claim 11, wherein the distance is at least about 0.5 mm.

13. An implantable sensor as in claim 11, wherein the distance is within the range of from about 0.3 mm to about 2.5 mm.

14. An implantable sensor as in claim 11, wherein the distance is sufficient to increase the blood flow velocity at the sensing surface to from about 125% to about 200% of the blood flow velocity immediately proximal to the support structures.

15. An implantable sensor as in claim 11, further comprising a transmitter mounted to at least one of the support structures, for transmitting information from the sensor to an external receiver.

16. An implantable sensor as in claim 15, wherein an inductive link supplies power to the transmitter.

17. An implantable sensor as in claim 11, further comprising a thin film rechargeable battery carried by the support structures.

18. An implantable sensor as in claim 11, wherein the support structures comprise enlargeable frames.

19. An implantable sensor as in claim 18, wherein the support structures comprise expandable tubular bodies.

20. An implantable sensor as in claim 11, wherein the support structures comprise balloon expandable stents.

21. An implantable sensor as in claim 11, wherein the support structures comprise self expandable stents.

22. An implantable sensor for sensing the presence of an analyte in a vessel, comprising:
    at least two substantially tubular support structures for anchoring the sensor in the vessel, each support structure having a side wall with a luminal side facing toward the center of the vessel and an abluminal side facing toward the wall of the vessel;
    a sensor housing carried by the support structures, the housing having a streamlined exterior configuration to minimize blood flow turbulence and located between the two support structures and positioned on the luminal side of the support structures;
    a power supply and electrical circuitry in the housing; and
    a sensing surface exposed to the exterior of the housing;
    wherein the sensing surface is positioned radially inwardly from the tubular support structures.

23. An implantable sensor as in claim 22, wherein the support structures are directly connected to one another.

24. An implantable sensor as in claim 22, wherein the support structures are not directly connected to one another.

25. An implantable sensor as in claim 22, further comprising a tubular sleeves surrounding the tubular support structures.

26. An implantable sensor as in claim 25, wherein the tubular sleeves are on the abluminal surface of the tubular support structures.

27. An implantable sensor as in claim 25, wherein the tubular sleeve is on the luminal surface of the tubular support structures.

28. An implantable sensor as in claim 25, wherein the tubular sleeves comprise ePTFE.

29. An implantable sensor as in claim 22, further comprising an analyte permeable membrane and an enzyme gel layer.

30. An implantable sensor as in claim 29, wherein the enzyme gel layer comprises glucose oxidase.

31. An implantable sensor as in claim 22, wherein the sensor comprises an amperometric sensor.

32. An implantable sensor as in claim 22, wherein the sensor comprises an electrode selected from the group consisting of oxygen electrodes, hydrogen peroxide electrodes, and electrodes with mediated electron transfer.

33. An implantable sensor for sensing the presence of an analyte in a vessel, comprising:
- at least two substantially tubular support structures for anchoring the sensor in the vessel, each support structure having a side wall with a luminal side facing toward the center of the vessel and an abluminal side facing toward the wall of the vessel;
- tubular sleeves surrounding the tubular support structures;
- a sensor housing carried by the support structures, the housing having a streamlined exterior configuration to minimize blood flow turbulence and located between two support structures;
- a power supply and electrical circuitry in the housing; and
- a sensing surface exposed to the exterior of the housing;
- wherein the sensing surface is positioned radially inwardly from the tubular support structures.

34. An implantable sensor as in claim 33, wherein the support structures are directly connected to one another.

35. An implantable sensor as in claim 33, wherein the support structures are not directly connected to one another.

36. An implantable sensor as in claim 33, wherein the sensor housing is positioned on the luminal side of the support structures.

37. An implantable sensor as in claim 33, wherein the tubular sleeves are on the abluminal surface of the tubular support structures.

38. An implantable sensor as in claim 33, wherein the tubular sleeves are on the luminal surface of the tubular support structures.

39. An implantable sensor as in claim 33, wherein the tubular sleeves comprise ePTFE.

40. An implantable sensor as in claim 33, further comprising an analyte permeable membrane and an enzyme gel layer.

41. An implantable sensor as in claim 40, wherein the enzyme gel layer comprises glucose oxidase.

42. An implantable sensor as in claim 33, wherein the sensor comprises an amperometric sensor.

43. An implantable sensor as in claim 33, wherein the sensor comprises an electrode selected from the group consisting of oxygen electrodes, hydrogen peroxide electrodes, and electrodes with mediated electron transfer.

44. An implantable sensor as in claim 33, wherein the sensing surface is spaced radially inwardly from the luminal side by a distance of at least about 0.2 mm, such that the velocity of blood in the vessel inhibits obstruction of the sensing surface.

45. An implantable sensor as in claim 33, wherein the distance is at least about 0.5 mm.

46. An implantable sensor as in claim 33, wherein the distance is within the range of from about 0.3 mm to about 2.5 mm.

47. An implantable sensor as in claim 33, wherein the distance is sufficient to increase the blood flow velocity at the sensing surface to from about 125% to about 200% of the blood flow velocity immediately proximal to the support structures.

48. An implantable sensor as in claim 33, further comprising a transmitter mounted to at least one of the support structures, for transmitting information from the sensor to an external receiver.

49. An implantable sensor as in claim 48, wherein an inductive link supplies power to the transmitter.

50. An implantable sensor as in claim 33, further comprising a thin film rechargeable battery carried by the support structures.

51. An implantable sensor as in claim 33, wherein the support structures comprise enlargeable frames.

52. An implantable sensor as in claim 51, wherein the support structures comprise expandable tubular bodies.

53. An implantable sensor as in claim 33, wherein the support structures comprise balloon expandable stents.

54. An implantable sensor as in claim 33, wherein the support structures comprise self expandable stents.

* * * * *

UNITED STATES PATENT AND TRADEMARK OFFICE
CERTIFICATE OF CORRECTION

PATENT NO. : 7,033,322 B2
APPLICATION NO. : 10/041036
DATED : April 25, 2006
INVENTOR(S) : James H. Silver It is certified that error appears in the above-identified patent and that said Letters Patent is hereby corrected as shown below:

On Title Page (56)

At column 2, line 17, after "6,477,395" delete "B1" and insert -- B2 --, therefore.

On Title Page (56)

At column 2, line 19, after "6,638,231" delete "B1" and insert -- B2 --, therefore.

On Title Page (56)

At column 2, line 21, after "4/2002" delete "Maron et al." and insert -- Meron et al. --, therefore.

On Title Page (56) OTHER PUBLICATIONS (pg 2)

At column 1, line 2, please delete "progession" and insert -- progression --, therefore.

At column 1, line 31, please delete "(Suppl 3)" and insert -- (Suppl. 3) --, therefore.

At column 3, line 9, after "Hall," delete "E.;" and insert -- E --, therefore.

At column 4, line 29, please delete "Kemer, et al." and insert -- Kerner, et al. --, therefore.

At column 7, line 19 (approx.), please delete "EMBODIMENT" and insert

-- EMBODIMENTS --, therefore.

At column 14, line 1, please delete "producing" and insert -- produce --, therefore.

At column 22, line 2, after "re-intervention" insert -- . --.

UNITED STATES PATENT AND TRADEMARK OFFICE
CERTIFICATE OF CORRECTION

PATENT NO. : 7,033,322 B2
APPLICATION NO. : 10/041036
DATED : April 25, 2006
INVENTOR(S) : James H. Silver It is certified that error appears in the above-identified patent and that said Letters Patent is hereby corrected as shown below:

At column 22, line 5, please delete "cab" and insert -- can --, therefore.

Signed and Sealed this

Twentieth Day of February, 2007

JON W. DUDAS
*Director of the United States Patent and Trademark Office*